United States Patent [19]

Judy et al.

[11] Patent Number: 5,030,200
[45] Date of Patent: * Jul. 9, 1991

[54] METHOD FOR ERADICATING INFECTIOUS BIOLOGICAL CONTAMINANTS IN BODY TISSUES

[75] Inventors: Millard M. Judy; James L. Matthews; Joseph T. Newman; Franklin Sogandares-Bernal, all of Dallas, Tex.

[73] Assignee: Baylor Research Foundation, Dallas, Tex.

[*] Notice: The portion of the term of this patent subsequent to Nov. 7, 2006 has been disclaimed.

[21] Appl. No.: 433,024

[22] Filed: Nov. 6, 1989

Related U.S. Application Data

[63] Continuation-in-part of Ser. No. 67,237, Jun. 25, 1987, Pat. No. 4,878,891.

[51] Int. Cl.$^5$ .............................................. A61M 37/00
[52] U.S. Cl. ........................................ 604/5; 424/529
[58] Field of Search ...................................... 604/4–6; 424/101, 529–531; 128/395

[56] References Cited

U.S. PATENT DOCUMENTS

| | | | |
|---|---|---|---|
| 4,613,322 | 9/1986 | Edelson | 354/321 |
| 4,614,190 | 9/1986 | Stanco et al. | 128/395 |
| 4,649,151 | 3/1987 | Dougherty et al. | 514/410 |
| 4,684,521 | 8/1987 | Edelson | 424/101 |
| 4,708,715 | 11/1987 | Troutner et al. | 604/6 |
| 4,878,891 | 11/1989 | Judy et al. | 604/5 |

*Primary Examiner*—Stephen C. Pellegrino
*Assistant Examiner*—Michael Rafa
*Attorney, Agent, or Firm*—Johnson & Gibbs

[57] ABSTRACT

A method for externally eradicating infectious pathogenic contaminants, such as enveloped viruses, bacteria, trypanosomal and malarial parasites, present in body tissues, such as blood, blood components, semen, skin, and cornea, before the treated body tissues are introduced into, or transplanted onto, the body of a human or an animal. Such method includes the steps of: (1) admixing an effective, non-toxic amount of photoactive compound, which has a selectively for binding to the infectious pathogenic biological contaminants present therein, with the body tissues outside the body to produce resulting body tissues; (2) maintaining the resulting body tissues in a suitable container in which there is no net mass transfer, and (3) irradiating the resulting body tissues in the container for an effective period of time with an effective level of radiation such that the radiation penetrates the resulting body tissues and eradicates the photoactive-compound-bound contaminants present in the resulting body tissues and produces a decontaminated body tissue suitable for introducing into, or transplanting onto, the body of a human or animal.

66 Claims, 7 Drawing Sheets

SYRINGE WITH BODY FLUID ATTACHED TO INFUSION PUMP

ATTACHED TO COLLECTING VIAL

REFLECTING MIRROR

REFLECTING MIRROR

METHOD FOR ERADICATING INFECTIOUS BIOLOGICAL CONTAMINANTS IN BODY TISSUES

BACKGROUND OF THE INVENTION

The present application is a continuation-in-part of U.S. patent application Ser. No. 07/067,237 now U.S. Pat. No. 4,878,891, filed on Jun. 25, 1987, which is incorporated by reference as if reproduced in its entirety.

1. Field of the Invention

The present invention relates generally to decontamination of body tissues; and more particularly, but not by way of limitation, to external eradication of infectious pathogenic biological contaminants from blood or blood products prior to intravenous injection of such blood or blood products into a patient's body.

The present invention also relates to external eradication of infectious pathogenic biological contaminants from skin, cornea or semen prior to transplanting or introducing of such tissues into the recipient's body.

2. Brief Description of the Prior Art

One of the many problems that plagues the use of blood transfusions is the transmission of agents causing infectious disease. A number of these infectious agents are of serious clinical importance in that such agents are not only dangerous to the recipient patients, but can also pose a danger to physicians, and other hospital personnel, handling the blood and blood products.

Many efforts have been made to ensure that the blood to be transfused is free of pathogenic biological contaminants. So far, screening of blood donors and blood samples is the only effective method to ensure that the blood to be transfused is not contaminated with infectious agents. Unfortunately despite screening techniques, infections still occur following blood transfusions.

U.S. Pat. No. 3,041,242 describes a process for eradication of virus contained in dried plasma wherein the dried plasma is heated at an elevated temperature for a length of time followed by applying a gas lethal to microorganisms, under high vacuum conditions. However, the method is not applicable to the treatment of human whole blood; and the viability of the dried plasma would most likely be impaired during the process.

It has been known for over 30 years that hematoporphyrin derivatives accumulate in neoplastic, embryonic, and regenerating tissues. Thus, injected hematoporphyrin has been found to have localized and fluoresced in several types of tumor induced in mice (Figge, F. H. J., Weiland G. S., Mangiollo, L. O.: Cancer Detection and Therapy. Affinity of Neoplastic, Embryonic, and Traumatized Tissues for Porphyrins and Metalloporphyrins. Proc. Soc. Exp. Biol. Med. 64: 640–641, 1948).

The red fluorescence of hematoporphyrin has also been observed under ultraviolet light in various malignant tumors in patients who had been given large doses of crude mixtures of hematoporphyrin compounds (hereinafter referred to as Hpd) (Rasmussen-Taxdal, D. S., Ward, G. E., and Figge, F. H. J.: Fluorescence of Human Lymphatic and Cancer Tissues Following High Doses of Intravenous Hematoporphyrin. Cancer 8: 78–81, 1955). As a result, methods have been developed to capitalize on the unique property of Hpd as a tumor marker in the detection and localization of different forms of cancer (King, E. G., et al., Hematoporphyrin Derivative as a Tumor Marker in the Detection and Localization of Pulmonary Malignancy, In Recent Results in Cancer Research, Vol. 82, Springer-Verlag, Berlin-Heidelberg, 1982, 90; Benson, R. D., et al, Detection and Localization of In Situ Carcinoma of the Bladder with Hematoporphyrin Derivative. Mayo Clinic Proc., 57: 548, 1982).

Although the unique photodynamic properties of Hpd, as well as its affinity toward tumor cells, had long been known, it was more than half a century later that the potential of using Hpd to selectively destroy tumor cells was explored. The bulk of the research on the use of Hpd to selectively destroy tumor cells in human has been reviewed by Dougherty et al. (Dougherty, T. J. et al., Photoradiation Therapy-clinical and Drug Advances. In Porphyrin Photosensitization, D. Kessel and T. J. Dougherty, Eds., Plenum Press, N.Y. PP. 3–13, 1983).

The emphasis on using Hpd as the photoactivating or light-activating compound in photoradiation of tumors is based on two important properties of Hpd. Firstly, as judged by fluorescence, Hpd is preferentially accumulated, and retained to a higher degree in malignant tumors than in surrounding normal tissue or benign tumors. Secondly, when properly photoactivated, Hpd causes the destruction of cells and tissue in which it resides. The generally accepted mechanism of cell kill by Hpd is that when activated by appropriate light, the Hpd can undergo an energy transfer process with oxygen to form a singlet oxygen, which subsequently oxidizes, hence kills the cells or tissues to which it has attached as a substrate. (Weishaupt, K. R., Gomer, C. J. and Dougherty, T. J., Identification of Singlet Oxygen as the Cytotoxic Agent in Photoinactivation of a Murine Tumor. Cancer Res. 36: 2326–2329, 1976).

Despite the enormous progress and research in the use of light-activated photosensitizer, such as Hpd, to pinpoint the location of malignant tumor cells and to eradicate them, relatively little work has been done to determine if such a photosensitizer will behave similarly toward virus, bacteria, fungi, protozoa, or other parasites.

U.S. Pat. No. 4,649,151 to Dougherty, et al., discloses the preparation, purification and utilization of tumor-selective, photosensitizing drugs (i.e. mixtures of porphyrins) in the localization and treatment of neoplastic tissue, such as tumors or cancers in patients and animals. A time delay of several hours to several days is required between injection of the drug and illumination in order for the drug to metabolically clear normal tissue and hence achieve the best therapeutic ratio of drug in tumor cells to drug in normal cells. One of the objects set forth in Dougherty, et al., is to provide a drug which is selective to certain pathogens within an animal or within blood, blood plasma or serum or fractions thereof and which permits photochemical destruction of the pathogens in vivo or in vitro. However, the reference contains no teaching or suggestion of the external purification of human tissues such as human blood, blood plasma, serum, semen, skin or cornea utilizing a mixture of porphyrins to eradicate infectious pathogens and to provide purified and sterilized human tissues such as human blood, blood plasma, human serum, semen, skin or cornea which can be infused or introduced into a patient's body.

The Dougherty, et al. patent also fails to demonstrate the tolerance of either human blood, human blood plasma, or human serum outside the body toward the drug. Moreover, no evidence was provided to demonstrate that either human blood, human blood plasma, human serum, or other human tissues outside the body remains unchanged after the irradiation of such blood, blood plasma, serum, or other tissues containing the described drug. Similarly, neither the effective range of concentrations of the described drug nor the effective range of radiation is disclosed for its use outside an animal or human body.

U.S. Pat. No. 4,614,190 to Stanco, et al. discloses an arrangement for effecting photoirradiation of tumor and cancerous tissues in human or animal body. The patent discloses the method of pulsing the electromagnetic energy to activate, in situ, administered hematoporphyrin derivative contained within the tissue in the body so that the surrounding flesh is not unduly affected.

This reference, however, neither teaches nor suggests the external purification of tissues such as blood, blood plasma, serum, semen, skin or cornea utilizing a mixture of porphyrins to eradicate infectious pathogens and to provide purified and sterilized tissues such as blood, blood plasma, serum, semen, skin or cornea which can be infused or introduced into the recipient's body.

The Stanco, et al. patent also fails to demonstrate the tolerance of either blood, blood plasma, serum, or other tissues outside the body toward the drug. Furthermore, no evidence was provided to demonstrate that either blood, blood plasma, serum, or other tissues outside the body remains undamaged after the irradiation of such blood, blood plasma, or serum, or other tissues containing the described drug. Similarly, neither the effective range of concentrations of the described drug nor the effective range of radiation is disclosed for its use outside an animal or human body.

Studies using fluorescence and laser techniques have suggested that hematoporphyin derivative (Hpd) would bind to parasites *Plasmodium berghei*, *P. vivax* and *P. falciparum*. Moreover, whole animal studies utilizing a mixture of Hpd and Chloroquine, an antimalarial drug, have reflected the reduction of the parasitemia in mice infected with Chloroquine resistant *P. berghei*. (F. Sogandares-Bernal, J. L. Matthews and M. M. Judy, HPD-Induced Reversal of Chloroquine Resistance to Malaria, a lecture presented at International Symposium on Malaria, held on Jun. 1-5, 1986, at Instituo Oswaldo Cruz, Rio de Janeiro, Brazil, also in press, Mem. Inst. Oswald Cruz).

A few investigators have reported photoinactivating bacterial viruses and animal viruses using heterocyclic dyes (Yamamoto, N., Nitrogen Fixation by A Facultatibe Bacillus, J. Bacteriology, 75: 403, 1958; Hiatt, C. W., et al: Inactivation of Viruses by the Photodynamic Action of Toluidine Blue, J. Immunology, 84: 480–84, 1960). The plaque formation capability of *Herpes simplex* virus has also been reported to be hampered by the treatment of virus in culture with a combination of a hematoporphyrin derivative and visible light. (Lewin, A. A., et al., Photodynamic Inactivation of *Herpes simplex* Virus by Hematoporphyrin Derivative and Light, Proc. Soc. Exp. Biol. Med. 163: 81–90, 1980).

Similarly, it has been reported that, in culture, the plaque formation by *Herpes simplex virus* type I, Cytomegalovirus, or measles virus is reduced, by more than 99%, by the combination effect of Hpd and Rhodamine B dyelaser light, with an energy density of 20 J/cm$^2$. On the other hand, the echovirus type 21, which lacks an envelope, is not affected under similar conditions (H. Skiles, M. M. Judy, and J. P. Newman, Photodynamic Inactivation of Viruses With Hematoporphyrin Derivatives, Abstract A 38, American Society for Microbiology, page 7, 1985). The combined effect of light and Photofrin II ™ on *Herpes simplex* virus type I grown in culture can be observed in a flow cell system made up of loops of transparent tubing attached to a glass slide, with a 1000 W Xeon light equipped with a red filter serving as the light source. (F. Sogandares-Bernal, J. L. Matthews, H. Skiles, M. M. Judy, and J. Newman, Photoactivation of *Herpes simplex* virus by Photofrin II and Light in A Flow Cell System, 1987 ASM Annual Meeting, Atlanta, Ga., 1–6 Mar. 1987).

Extracorporeal treatments of certain noninfectious cancers have been known for more than a decade. (H. Hyden, L. E. Gelin, S. Larsson, and A. Saarne, A New Specific Chemotherapy: A Pilot Study With An Extracorporeal Chamber. Rev. of Surgery (Philadephia), 31: 305–320, 1974; H. Wolf, E. Langvad, and H. Hyden, The Clinical Course In Patients With Renal Carcinoma Subjected To Extracorporeal Immunoadsorption, British J. Urology, 53: 89–94, 1981). Recently, it was reported that the activity of a noninfectious cancer, but nevertheless potentially deadly, cutaneous T-cell lymphoma, could be controlled by extra corporeal photochemotherapy. In the therapy, after patients were orally given 8-methoxypsoralen, blood was removed from the patient and the lymphoctye-enriched blood fraction was exposed to ultraviolet A. Subsequently, the damaged lymphocyte-enriched blood fraction was returned to the body of the patient. An immune reaction to the infused damaged cells then restricted the activity of the abnormal cancer cells in the patient's body. (R. Edelson, et al., Treatment of Cutaneous T-Cell Lymphoma by Extracorporeal Photochemotherapy, New England J. Medicine, 316: 297–303, 1987).

The purpose of the extracorporeal photochemotherapy as reported by Edelson, et al., was not to damage as many cells as possible outside the patient's body. Rather, only a small fraction of the cells was damaged which was then reintroduced into the patient's body to serve as a "vaccine" for triggering an immune reaction in the body.

Despite the progress in photochemotherapy, no work, however, has been reported concerning the utility of such method to eradicate viruses present either in human whole blood or in other body tissues outside the body. Similarly, no one has reported the use of photoinactivation in a clinical setting to remove infectious agents, such as viruses, bacteria, fungi and protozoa, from human whole blood used for transfusion.

Hepatitis-B virus causes a hepatitis infection which may develop into cirrhosis in which the liver becomes a mass of fiber-like tissue. In hepatitis, liver function is impaired and, in some cases, the condition can be fatal. There are approximately 200,000 cases of reported hepatitis infections per year in this country. In addition, there may be as many as a few million carriers of hepatitis.

The human T-lymphotropic retrovirus (HTLV) is the cause of acquired immune deficiency syndrome (AIDS) which is invariably fatal. So far, the AIDS virus has infected more than a million people in this country alone. About one-third to one-half of the infected individuals will develop the disease. Worst yet, because the AIDS virus has a long and undeterminate period of incubation, a person can unknowingly carry and spread the deadly disease for years. The invariably fatal viral disease AIDS can be transmitted by the exchange of body tissues or body fluids such as blood, blood products, or semen. Indeed, hemophiliacs and other receiving blood transfusions account for about 3% of the reported AIDS cases in this country between 1981 and late 1986. Artificial insemination, organ transplant, and transplant of skin, cornea and other tissues can also transmit this fatal viral disease.

People infected with viruses may carry these agents or their particles in their blood. Likewise, people attacked by infectious diseases often carry pathogenic microorganisms or other contaminants in their blood. Consequently, blood donated or sold to blood banks may be contaminated with virus or other biological and pathogenic contaminants.

Most blood samples are now being tested for the presence of certain virus. These tests usually involve the determination of the presence of antibodies to various viruses or the viral antigen itself, such as HBsAg. Although most of the tests employed to test blood samples are generally quite accurate, they are not infallible. Also, due to cost considerations, not all blood is tested for the presence of pathogenic contaminants, including viruses. Most importantly, because antibodies do not form immediately after exposure to the virus, a newly infected person may unknowingly donate blood after becoming infected but before the antibody has a chance to manifest a positive test. It has also been documented that some people infected with certain viruses simply do not produce detectable antibodies against them.

A large number of diseases, some of which are either fatal or of serious clinical importance, can be transmitted by transfusion. Since pathogenic organisms are found in different fractions of whole blood, risks of post-transfusion diseases vary depending on the blood product or component used. In general, the risk for any disease is directly proportional to the volume of blood transfused and to the numbers of infectious organisms contained therein.

It is clear that despite screening techniques, infections with viruses and other biological pathogenic contaminants still occur following blood transfusions. In the setting of clinical medicine, the processing and handling of body fluids, such as blood, imposes a threat of a number of possible infections to physicians and other hospital workers, and patients. Currently, there is no effective procedure for decontaminating the infected body fluid, such as human whole blood or its formed elements.

It is, therefore, highly desirable to have a safe and economical method and apparatus that will eradicate pathogenic viruses, microorganisms, or parasites present in human whole blood or blood products before such products are infused into a recipient, hence, infecting the recipient with such disease producing agents. At the same time, properly decontaminated blood will also spare the daily threat of infections to hospital personnel who must handle these body fluids. This need is even more acute in a blood bank where donor blood and blood products are stored and processed.

It is equally desirable to have a safe and economical method and apparatus that will eradicate pathogenic viruses, microorganisms, or parasites present in human or animal tissues, such as skin, cornea, and semen, before such tissues are introduced or transplanted into a recipient, hence, infecting the recipient with such diseases.

Since there is so far no cure for AIDS, it is also desirable to have a safe method and apparatus to reduce the viremia in AIDS patients to prolong the lives of such patients.

It is toward such goals that the present invention is directed.

SUMMARY OF THE INVENTION

According to the present invention an efficient and economical method for treating body tissues to eradicate infectious pathogenic biological contaminants, such as envelope-containing viruses, bacteria, malarial, trypanosomes, and other parasites, which may be present in said body tissues is provided wherein the contaminants are eradicated prior to introduction of the treated body tissues into the body of a patient. Broadly, the method comprises:

(a) introducing or admixing an effective, non-toxic amount of a photoactive compound with the body tissue to produce a resulting body tissue, the photoactive compound having a selectivity for binding to the infectious pathogenic biological contaminants present in the body tissue;

(b) maintaining the resulting body tissue in a suitable container in which there is no net mass transfer; and (c) irradiating the resulting body tissue in the container for an effective period of time with an effective level of radiation such that the radiation penetrates the resulting body tissue and eradicates the photoactive-compound-bound contaminants and produces a decontaminated body tissue suitable for introduction into the body of a patient.

An object of the present invention is to provide an improved method for externally eradicating infectious pathogenic biological contaminants from blood and blood products.

Another object of the present invention is to provide an efficient and economical method to externally eradicate infectious pathogenic biological contaminants from blood and blood products in a container so that the blood and blood products are safe for introduction into the body of a patient.

Still another object of the present invention is to provide an efficient and economical method for externally eradicating infectious pathogenic biological contaminants from blood or blood products so that the blood or blood products are safe for handling.

Another object of the present invention is to provide an effective and economical method for external eradication of pathogenic enveloped viruses, other microorganisms, or other pathogenic biological contaminants in tissues intended for transplantation to humans.

Yet another object of the present invention is to provide an effective and economical method for external eradication of pathogenic enveloped viruses, other microorganisms, and parasites, or other pathogenic biological contaminants in protein and other materials intended for intravenous administration to humans or animals.

Other objects, advantages and features of the present invention will become clear from the following detailed description when read in conjunction with the drawings and appended claims.

BRIEF DESCRIPTION OF THE DRAWINGS

FIG. 3-a is a diagram showing a three-dimensional rectangular coordinate system for the irradiation cell of FIG. 3.

FIG. 4-a is a diagram showing a three-dimensional rectangular coordinate system for the irradiation cell in FIG. 4.

FIG. 5-a is a diagram showing a three-dimensional rectangular coordinate system for the irradiation cell in FIG. 5.

DESCRIPTION OF THE PREFERRED EMBODIMENT

Figure 1:
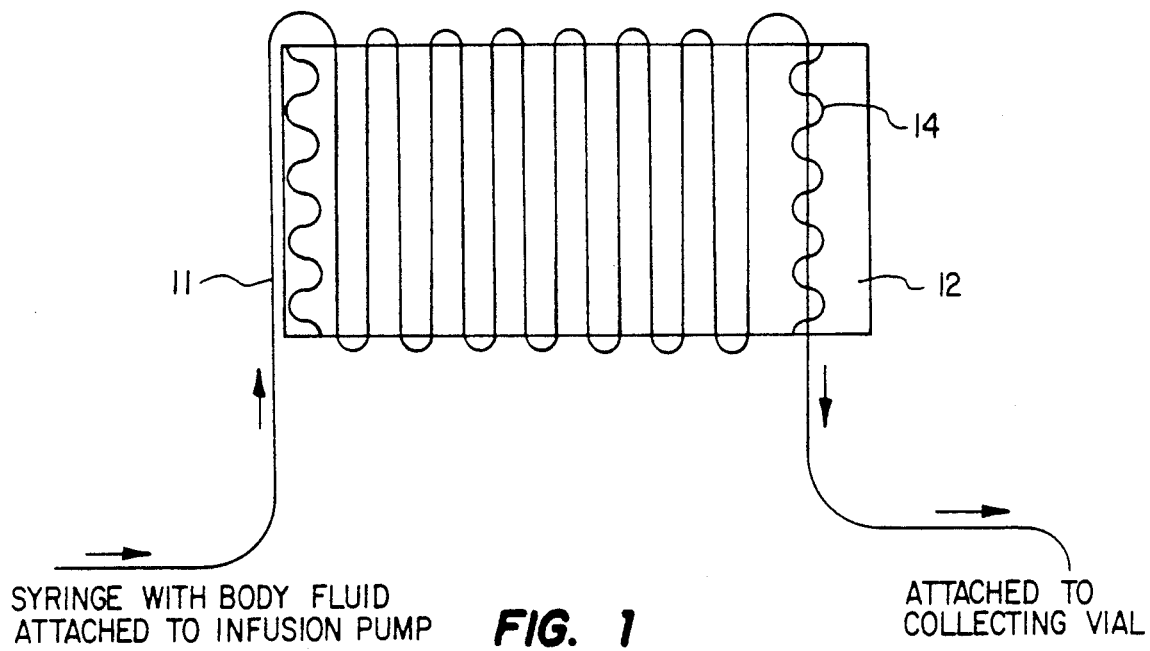
FIG. 1 is a schematic representation of a cell assembly having a predetermined flow path in the form of a flexible transparent tubing wherein fluids passing along the flow path are exposed to radiation.

The present invention provides a method for externally eradicating infectious pathogenic contaminants, such as enveloped viruses, microorganisms, parasites, bacteria and the like, from body tissues that the likelihood of a person becoming infected as a result of receiving a transfusion or transplantation of the body tissue is substantially eliminated or at minimum the parasite or infectious agent burden of the tissue is considerably reduced.

The term "body tissue" as used herein is to be understood to include "body fluid", packed red blood cells, packed white blood cells, platelets, cryo precipitate from blood plasma, other plasma proteins, skin, cornea, and other tissue from an animal or a human.

The term "body fluid" as used herein is to be understood to include whole blood, any formed elements of the blood, blood plasma, serum, fluids containing said components, fluids from plasmapheresis, plasma fibrinogen, cryo-poor plasma, albumin, gamma globulins, semen, and other fluids introduced or intravenously injected into the body of a patient or an animal using known administration techniques. The "body fluid" as used herein is to be understood to include body fluid prior to, or after, physical as well as chemical fractionation, separation or freezing.

The term "external" as used herein is to denote outside the animal or human body. As is known in the art, the term "extracorporeal" means outside of, or unrelated to, the body or any anatomical "corpus".

The words "no net mass transfer" as used herein are to denote the condition in which the body tissue that is maintained or stored in a container neither enters nor leaves the container while being irradiated. In the case of body fluids, the body fluids do not flow in and out of the container during the process of illumination. The body tissues can be either kept static in the container or subjected to agitation or movement. Optically transparent or "thin" body tissues can be irradiated in the container under static conditions. On the other hand, in the irradiation of optically "thick" or non-transparent body tissues, agitation may be required. Optically "thick" or non-transparent body tissues are those that absorb and scatter light appreciably and will not allow light to penetrate. Agitating the optically "thick" or non-transparent body tissues in the container will promote the mixing, and hence the binding, of the body tissues with the photoactive compound. Moreover, agitation will enhance the probability of having every cell in, and every part of, the body tissues exposed to incident radiation.

The words "illuminated with light" and "irradiated with radiation" are used interchangeably.

The method of the present invention provides for the external decontamination of body tissues containing infectious pathogenic biological contaminants such that the body tissues possess the desired therapeutic properties and viability as normal, untreated body tissues. Broadly, the method for treating body tissues to eradicate infectious pathogenic biological contaminants which may be present therein comprises:

(a) admixing an effective, non-toxic amount of a photoactive compound with the body tissue to produce a resulting body tissue, the photoactive compound having an affinity for infectious pathogenic biological contaminants in the body tissue such that the photoactive compound is selectively bound to such contaminants;

(b) maintaining the resulting body tissue in a suitable container in which there is no net mass transfer; and (c) irradiating the resulting body tissue in the container with an effective level of radiation for a prescribed period of time so that the radiation penetrates throughout the resulting body tissue in the irradiated path and exposes the photoactive-compound-bound contaminants to the radiation so as to eradicate such contaminants and produce a sterile body tissue.

Photoactive compounds which are selective for infectious pathogenic biological contaminants, and which can be used in the eradication of such contaminants in accordance with the present invention, must satisfy the following criteria:

(1) normal body tissues remain undamaged in an environment outside of a human body when subjected to a combined action of irradiation and the photoactive compound in levels effective to eradicate or destroy the infectious pathogenic biological contaminants present in such body tissues;

(2) the photoactive compound is preferentially bound to the infectious pathogenic biological contaminants either directly or indirectly by an antibody bridge or other linking molecule; and (3) upon irradiation, the photoactive compound eradicates or destroys the infectious pathogenic biological contaminants to which the photoactive compound has bound.

Photoactive compounds meeting the foregoing criteria comprise porphyrins or hematoporphyrins. Such compounds contain groups of pyrroles or substituted pyrroles combined in a specific pattern. The basic structural grouping consists of phlorin or a group of four pyrroles or combinations of pyrroles and substituted pyrroles combined into a larger ring structure. Two such rings are covalently bonded to form a pair of units each having four pyrrole groups or four groups at least some of which are pyrroles or substituted pyrroles. The resultant molecules have an absorption spectrum within the range of wavelengths of from about 350 nm and about 1200 nm, and more desirably from about 350 nm to about 700 nm.

The preparation and purification of photoactive compounds comprising porphyrin and hematoporphyrins is disclosed in U.S. Pat. No. 4,649,151; and certain of such photoactive compounds are commercially available from Johnson & Johnson as "Photofrin II TM" (Hpd) and "Photofrin II TM" (a compound containing approximately 90% dihematoporphyrin ether, DHE).

The molecular structure of at least a portion of such photoactive compounds which render such compounds useful in the practice of present invention is as follows:

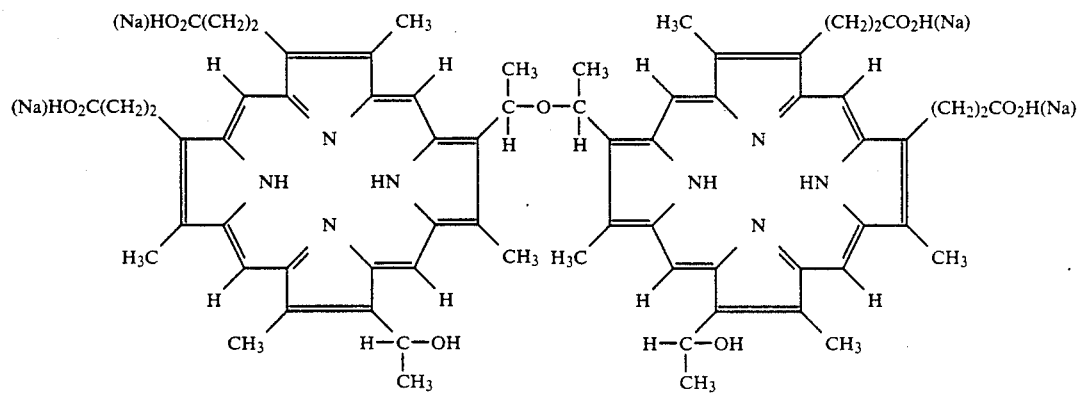

said molecules with said formula being fluorescent, photosensitizing, having the capability of selectively binding to said pathogenic biological contaminants, forming a high molecular weight aggregate with absorption peaks in the visible spectrum in water at approximately 365, 505, 537, 575, and 615 nanometers, absorption peaks in the infrared spectrum at approximately 3.0, 3.4, 6.4, 7.1, 8.1, 9.4, 12 and 15 microns, absorption peaks in carbon-13 nuclear magnetic resonance study at at least approximately 9.0, 18.9, 24.7, 34.5, 62, 94.5, 130-145, 171.7 ppm relative to a 37.5 ppm resonance peak of dimethyl sulfoxide and additional absorption peaks in carbon-13 nuclear magnetic resonance study at approximately 27.9 ppm and 68.4 ppm relative to the resonance peak of tetramethylsilane in deuterated chloroform solvent; and at least 50 percent of the porphyrins in said mixture being of said molecule having said molecular formula.

The effective, non-toxic amount of the mixture of porphyrins admixed with the body tissue externally can vary widely, depending to a large degree on the amount of infectious pathogenic biological contaminants present or suspected to be present in the body tissue. However, to be effective the amount of the mixture of porphyrins utilized should be in excess of the amount of such contaminants to insure that sufficient mixture of porphyrins is present to bind all of the contaminants present in the body tissue. Generally, however, the amount of mixture of porphyrins admixed with the body tissue to satisfy the above requirement is from about 0.1 to about 50 micrograms of the mixture of porphyrins per milliliter of body fluid. Desirably, the amount of the mixture of porphyrins used is from about 2 to about 50 micrograms per milliliter of body fluid.

To eradicate the infectious pathogenic biological contaminants which have been bound to the photoactive compounds, the resulting mixture of body fluid and the photoactive compound is subjected to radiation, while maintaining the resulting mixture under flow conditions during exposure to the radiation.

Any suitable source can be employed to irradiate the photoactive-compound-bound contaminants provided such source produces sufficient radiation to activate the photoactive compound so as to eradicate or destroy such contaminants bound to the compound and sufficient energy to insure complete penetration of the radiation through the body fluid being treated, so that the treated body fluid is free of such contaminants. The operable source employed to irradiate the resulting fluid has a wavelength of from about 350 nm to about 1000 nm and an energy density of from about 0.1 J/cm² to about 50 J/cm². Desirably, the irradiating source has a wavelength from about 600 nm to about 700 nm with an energy density from about 1 to 20 J/cm². Suitable sources which satisfy such requirements are a Xenon 1000 W light fitted with infra-red blocking filters and 630±10 nm band pass filter or a laser light source emitting radiation within (around 630 nm) the absorption spectrum of the photoactive compound and having the desired energy density. Another suitable source is a quartz halogen lamp.

As previously stated, the resulting mixture of body fluids and the photoactive compound is subjected to radiation while being maintained in a container. The agitation enhances the mixing of the photoactive compound with the body fluid to insure that the contaminants in the body fluids are sufficiently bound to the photoactive compound; and the agitation further enhances exposure of the chemically bound contaminants to the desired level of radiation to insure eradication of such contaminants. The desired agitation, mixing and exposure to irradiation of the resultant mixture of body fluids can be achieved by moving the container in which the resultant mixture of body fluids are maintained and stored. The container can be moved in a reciprocatory translational motion such as laterally, vertically, or circularly. Some containers can even be moved in a reciprocatory rotational motion along the three coordinate axes of the container. Alternatively, an agitating means comprising a movable inert agitating object, such as a stirrer or a bar-shaped or ball-shaped agitator, can be used to promote and enhance the agitation. Preferably, the agitating object will be placed inside the container. The agitating means can be sonic, mechanical, electrical, or magnetic. However, the level of agitation of the body fluids being treated must be maintained below a level where shearing of the body fluids or cells would occur.

A suitable container can be an open container, or a closed container. It can be a bag, a tube, a box, a petri dish, or others. Generally, the container is made up of inert transparent materials, such as plastics, other polymeric materials, glasses, or quartz. For an open container, it need not be made up of transparent materials. The internal surface of the container can either be smooth, roughened or rippled. The roughened or rippled surface can enhance the desired mixing. Further, to insure that the body fluids in such a container are exposed to a sufficient level of radiation to eradicate the contaminants, the body fluids are exposed to a radiation density of about 5 J/cm$^2$.

As will become apparent, the desired exposure time can be readily controlled by the surface of body tissue that is exposed, in combination with the agitation rate of the body tissue. However, care must be exercised to insure that irradiating of body tissue to eradicate or destroy the contaminants does not heat the body tissue to a temperature sufficient to destroy the viability of the purified body tissue. Care must also be taken to insure that the agitation is not violent enough to cause damage to cells.

For the extracorporeal treatment of the blood of a patient infected with infectious biological contaminants, a dosage from about 0.5 mg to about 40 mg of a mixture of porphyrins per kg of the body weight of the patient is commonly used. The mixture of porphyrins can be administered to the patient either by oral or intravenous route. The mixture of porphyrins can be given from about one hour to about one week prior to the start of irradiating the blood removed from the patient's body. Generally, the blood that contains the mixture of porphyrins bound to the infectious biological contaminants is removed from the body of the patient and maintained in a container in which there is no net mass transfer. The blood is then agitated and irradiated with a light source having a wavelength of about 600 to 700 nm. The energy density most often used to irradiate the blood in the flow cell is from about 1 J/cm$^2$ to about 50 J/cm$^2$.

Alternatively, the patient's blood that is infected with infectious biological contaminants is removed from the patient's body and then admixed with a sterile saline solution containing an effective amount of a mixture of porphyrins to bind to all the infectious contaminants. The saline solution containing the mixture of porphyrins is added at a rate that will maintain the concentration of the mixture of porphyrins in the resulting fluid to be from about 0.1 to about 50 micrograms per milliliter of the infected blood. The preferred concentration, however, is from about 2 to about 50 micrograms per milliliter of infected blood. The resulting mixture is then agitated and irradiated in the a container. The operable light source for irradiation has a wavelength of about 600 to 1000 nm, although the preferred wavelength range is from about 600 to 700 nm. The operable energy density that can be used to irradiate the resulting fluid in the flow cell is from about 1 to 50 J/cm$^2$, but the preferred range is from about 1 to 20 J/cm$^2$.

Due to diapedesis, a natural phenomenon in which some lymphocytes pass through the intact walls of blood vessels and mix with other tissue fluids, not all lymphocytes will be available, at one time, for the extracorporeal treatment. Accordingly, the patient undergoing such extracorporeal treatment has to be subjected to a series of extracorporeal treatments with an interval of a few days ranging from 2 to 7 days. The duration of one extracorporeal treatment can range from about 3 to about 10 hours.

A pump is usually not required for the operation of extracorporeal treatment. At a systolic blood pressure of 130 to 170 mm Hg, the blood can flow through a flow cell at a rate of about 80 to 140 ml/min through a channel of typical cross-section of 0.7×100 mm with a length of about 150 to 200 cm. The flow cell for this procedure can be constructed to contain a total of about 120 ml of blood.

As discussed above, there is currently no cure for AIDS. Without an effective treatment, AIDS victims live, on the average, about 2 years after diagnosis. It is only logical that if the viremia of an AIDS victim can be reduced, such a victim would have a better chance of staying alive longer, or at least the life in this victim can be improved. The extracorporeal photochemical treatment of infected blood from an AIDS patient can fulfill such a goal because the method described herein has been shown to eradicate human immunodeficiency virus which causes AIDS.

Where the body tissue is not in fluid form, said tissue is excised from the donor as a thin layer that is translucent to light and is then suspended in a physiologically acceptable saline solution containing an effective, nontoxic amount of the photoactive compound. The resulting suspension is then subjected to radiation while maintaining the resulting suspension under gentle agitation during exposure to the radiation. The gentle agitation would enhance the mixing of the photoactive compound and the tissues suspended in the solution to insure that the infectious biological contaminants in the body tissues are sufficiently bound to the photoactive compound; and the gentle agitation further enhances exposure of the chemically bound contaminants to the desired level of radiation to insure eradication of such contaminants. The gentle agitation can be achieved by placing the entire irradiation assembly in a laboratory shaker. Thus, the cell assembly can be gently agitated while the body tissues suspended in sterile solution are being irradiated.

The operative amount of the mixture of porphyrins to be added to the suspension of body tissue in a physiologically acceptable saline solution is from about 0.1 to about 50 micrograms per milligram of the suspended body tissue. Desirably, however, the amount of the mixture of porphyrin added is from about 2 to 50 micrograms per milligram of the suspended body tissue. The source employed to irradiate the resulting suspension has a wavelength of from about 350 nm to about 700 nm and an energy density of from about 0.1 J/cm$^2$ to about 20 J/cm$^2$. Desirably, the irradiation source has a wavelength from about 600 nm to about 700 nm with an energy density from about 1 to about 20 J/cm$^2$.

As previously set forth, the method of the present invention provides an economical and efficient means for externally eradicating infectious pathogenic biological contaminants from body tissues so that the likelihood of a person becoming infected as a result of a transfusion or transplantation is substantially eliminated. The contaminants which can be effectively eradicated from a body fluid using the present invention are the enveloped viruses, other microorganisms, including other parasites and bacteria. The term "enveloped virus" in all cases but one is understood to be a virus of which is encased within a modified host cell membrane, except for the Pox-virus which produce their own envelope. Typical of such enveloped viruses are: Cytomegalovirus, *Herpes simplex* virus, Pox virus, human immunodeficiency virus, Epstein-Barr virus, and others as set forth in Table I. Other viruses include Dengue virus and yellow fever virus.

Microorganisms, parasites and bacteria which can be effectively eradicated by the method of the present invention include: *Plasmodium vivax, P. malariae, P. falciparum, P. ovale,* and *Trypanosoma cruzi; Bacillus subtilis, Streptococcus faecalis,* and *Borrelia burgdorferi,* the bacteria that cause Lyme disease; *Babesia microti;* Leptospira; Borrelia; Haemobartonella; and Barcherlichia.

In order to more fully describe the method for eradicating infectious pathogenic biological contaminants from body fluids in accordance with the present invention, reference is now made to FIG. 1 through FIG. 16 of the drawings wherein schematic representations of cell assemblies and containers useful in the practice of the invention are set forth.

In irradiating blood or blood products to achieve photodynamical killing of infectious pathogens with the preferred embodiment, a closed container with uniform thickness of surfaces containing the blood or blood products is illuminated with light of essentially uniform intensity and of appropriate wavelength to initiate photosensitization. Alternatively, the blood or blood products can be maintained in an open container and illuminated with light of essentially uniform intensity and of appropriate wavelength to initiate photosensitization. With such uniform irradiation, all units of blood or blood products maintained and stored in the container receive essentially the same incident light fluence. In this way, fluid flow and illumination conditions, demonstrated experimentally to result in killing of the pathogen, can be accurately reproduced.

Similarly, the irradiation cell for the irradiation of body tissues suspended in a physiologically acceptable saline solution has boundary surfaces of uniform thickness. The irradiation cell assembly is also illuminated with light of essentially uniform intensity and of appropriate wavelength to initiate photosensitization. With such uniform irradiation, all areas of the body tissues receive essentially the same incident light fluence. Hence, the results obtained can be accurately reproduced.

TABLE I

The following are enveloped viruses as divided into family and common species or genus:

| Family | Common Species or Genus |
|---|---|
| Herpesviridae | Human herpes simplex virus types types I and II |
| | bovine *mammillitis virus* |
| | herpes B virus of monkeys |
| | *pseudorabies virus* |
| | equine *rhinopneumontis virus* |
| | *varicella-zoster virus* |
| | human cytomegaloviruses |
| | murine cytomegaloviruses |
| | Epstein-Barr virus |
| | Baboon herpes virus |
| | Chimpanzee herpesvirus |
| | Marek's disease herpes virus |
| | Hinze virus |
| | Turkey herpes virus |
| | *Herpesvirus ateles* |
| | *Herpesvirus saimiri* |
| | Infectious bovine *rhinotracheitis virus* |
| Iridoviridae | Aftrican swine fever virus |
| | Frog virus group (Ranavirus) |
| | Iridovirus |
| | Chloriridovirus |
| Poxviridae | *vaccinia virus* |
| | smallpox virus |
| | cowpox virus |
| | monkeypox virus |
| | buffalopox virus |
| | camelpox virus |
| | ectromelia of mice virus |
| | rabbitpox virus |
| | Orf virus |
| | virus of milker's node |
| | avipoxvirus |
| | sheep pox virus |
| | goat pox virus |
| | lumpy skin disease (Neethling) virus |
| | myxoma virus of hares |
| | fibroma viruses of rabbits |
| | fibroma viruses of squirrels |
| | swinepox virus |
| | Yaba monkey virus |
| | *molluscum contagiosum* virus |
| Hepadnaviridae | human hepatitis B virus (HBV) |
| | woodchuck hepatitis virus |
| | ground squirrel hepatitis virus |
| | duck hepatitis virus |
| Orthomyxoviridae | Influenza virus, types A, B, and C |
| Paramyxoviridae | Newcastle disease virus of fowl |
| | human parainfluenza viruses |
| | Sendai virus |
| | mumps virus |
| | paramyxoviruses |
| | measles virus |
| | rinderpest virus of cattle |
| | canine distemper virus |
| | peste-des-petits-ruminants virus of sheep and goats |
| | respiratory syncytial virus of man |
| | bovine respiratory syncytial virus |
| | pneumonia virus of mice |
| Rhabdoviridae | rabies virus |
| | vesicular *stomatitis virus* of: horses, cattle and swine |
| | *chandipura virus* |
| | lyssavirus |
| | duvenhage virus |

TABLE I-continued

The following are enveloped viruses as divided into family and common species or genus:

| Family | Common Species or Genus |
|---|---|
| | Lagos bat virus |
| | mokola virus |
| Bunyaviridae | bunyavirus (Bunyamwera, Bwamba, California, Capim, Guama, phlebovirus koongol, patois, simbu and tete viruses) |
| | sandfly fever virus |
| | Rift Valley fever virus of sheep and ruminants |
| | Nairovirus |
| | Crimean-Congo hemorrhagic fever viruses |
| | Uukuvirus |
| | Uukuniemi virus |
| | Hantaan virus |
| | Korean hemorrhagic fever virus |
| Filoviridae | ebalo virus |
| | Marburg virus |
| Nodaviridae | Nodamura virus |
| Togaviridae | Alphaviruses |
| | aura virus |
| | Chikungunya virus |
| | eastern equine encephalitis virus |
| | getah virus |
| | mayaro virus |
| | middleburg virus |
| | mucamba virus |
| | ndumu virus |
| | O Nyong-nyong virus |
| | pixuna virus |
| | ross river virus |
| | semliki forest virus |
| | sindbis virus |
| | una virus |
| | Venezuelan equine encephalitis virus |
| | western equine encephalitis virus |
| | Whataroa virus |
| | rubella virus |
| | mucosal disease virus |
| | border disease virus |
| | hog cholera virus |
| Flaviviridae | flavivirus |
| | Brazilian encephalitis virus |
| | Bussuguara virus |
| | dengue virus |
| | iiheus virus |
| | Israel turkey meningoencephalitis virus |
| | Japanese B encephalitis virus |
| | kunjin virus |
| | Kyasanur forest disease virus |
| | langat virus |
| | louping ill virus |
| | modoc virus |
| | Murray valley encephalitis virus |
| | ntaya virus |
| | omsk hemorrhagic fever virus |
| | powassan virus |
| | St. Louis encephalitis virus |
| | spondwnei virus |
| | tick-borne encephalitis |
| | Uganda S virus |
| | US bat salivary gland virus |
| | wesselsbron virus |
| | west nile fever virus |
| | yellow fever virus |
| | zika virus |
| | european tick-borne encephalitis |
| | far eastern tick-borne encephalitis virus |
| | Russian tick-borne encephalitis |
| Retroviridae | type C oncovirus group |
| | type B oncovirus group |
| | type D retrovirus group |
| | avian complex leukemia virus |
| | Rous sarcoma virus |
| | murine complex leukemia virus |
| | mouse sarcoma virus |
| | murine mammary tumor virus |
| | feline complex leukemia virus |
| | feline complex sarcoma virus |
| | woolly monkey sarcoma virus |
| | Gibbon leukemia virus |
| | mason-Pfizer virus |
| | hamster leukemia virus |
| | rat leukemia virus |
| | bovine lymphoma virus |
| | human T cell leukemia viruses: types 1 and 2 etc. |
| | *spumavirinae*: syncytial and foamy viruses of humans, monkeys, cattle, cats |
| | visna virus of sheep |
| | Maedi virus |
| | progressive pneumonia viruses of sheep |
| | *human immunodeficiency viruses (includes HTLV III/LAV) HIV, HTLV IV, LAV-2, STLV-III$_{AGM}$ |
| Arenaviridae | Junin virus |
| | lassa virus |
| | machupo virus |
| | pichinde virus |
| | lymphocytic choriomeningitis virus |
| | lassa fever virus |
| | pichinde virus |
| | arenavirus |
| Other virus-like agents viroids-prions | kuru virus |
| | Creutzfeldt-Jakob disease virus |
| | scrapie virus |
| | transmissible mink encephalopathy |
| | Aleutian disease of mink |

*NOTE:
under Retroviridae
HTLV III, human T-lymphotropic virus type III
LAV, Lymphadenopathy virus
HIV, human immunodeficiency virus
STLV-III$_{AGM}$ simina T-lymphotropic virus type III
HTLV IV, human T-lymphotropic virus type IV
HTLV III and LAV are now usually referred to as HIV Red blood cells (rbc) containing hemoglobin absorb and scatter light appreciably. In normal human whole blood, the concentration of rbc is approximately 46% by volume. Thus, in normal human whole blood, the attenuation of light intensity I "Zee Zero", Z0, penetrating from an illuminated surface as described by Beer's law is given after penetration to depth Z by $$I = I_{z0} \exp[-(A+S)Z]$$

where $I_{z0}$ is the light intensity at the illuminated surface and the constants A and S are the absorption constant and scattering constant, respectively. For blood, these are, approximately, $A = 5$ cm$^{-1}$ and $S = 10$ cm$^{-1}$ at 630 nm light wavelength. Using these numbers, it can be seen that the Beer's Law light intensity decreases to about 0.47, 0.22, and 0.10 of $I_{z0}$ at depths of 0.05, 0.1, and 0.15 cm, respectively. Thus, with depth, whole blood or thick suspensions of rbc becomes optically thick. One way to overcome the thickness is to treat an optically thin layer of blood having very large lateral surface extent under static fluid conditions. Alternatively, the same result can be achieved by exposing an appreciable volume of thin layer of blood to the light, each small volume element of blood is brought to the surface having an optically thin depth for light exposure. This alternative way can be brought about through fluid mixing with no net fluid volume displacement from the container, no net mass transfer. It is necessary for each small volume to be exposed to a sufficient light fluence (J/cm$^2$) for photosensitized inactivation of infectious agents to occur. This requirement necessitates a minimum residence time within the near surface fluid region by repetitive and adequate mixing motion. Such mixing motion can be attained in a number of different ways. Generally, blood or blood components are retained inside a sterile bag without having the sterility of an enclosed system broken at anytime subsequent to collection from the donor. Then the bag is subjected to movement to create the mixing motion. Alternatively, an agitating object inside the bag can be used to create the mixing motion.

FIG. 1 shows a schematic diagram of a flow cell used in the original experiments. Whole blood or other body fluid was infused via a syringe driven by an infusion pump. The blood or body fluid was constrained to flow through a flexible transparent plastic tube, 11, which was looped along the planar surface of a 2 in.$\times$2 in. area of transparent glass slide, 12, which served to support the tube in a plane perpendicular to the irradiating light beam. The tube was attached to the glass slide 12 by epoxy glue shown as 14. Tube diameter was 0.05 cm and the length of the tube illuminated was 40 cm. Irradiation was essentially uniform with irradiance $I_o$ of $1.04\times10^{-2}$ w/cm$^2$ at 630$\pm$5 nm wavelength. Flow rate of body fluid was $9.8\times10^{-4}$ cm$^3$/min. The flow time for each unit of volume element of body fluid within the illuminated region was about 8 minutes. Irradiation of the 2 in.$\times$2 in. planar area occupied by the looped flow tube for the 8 min. flow time resulted in a fluence of $E_o=5$ J/cm$^2$ delivered to the planar area of the looped tube.

Figure 2:
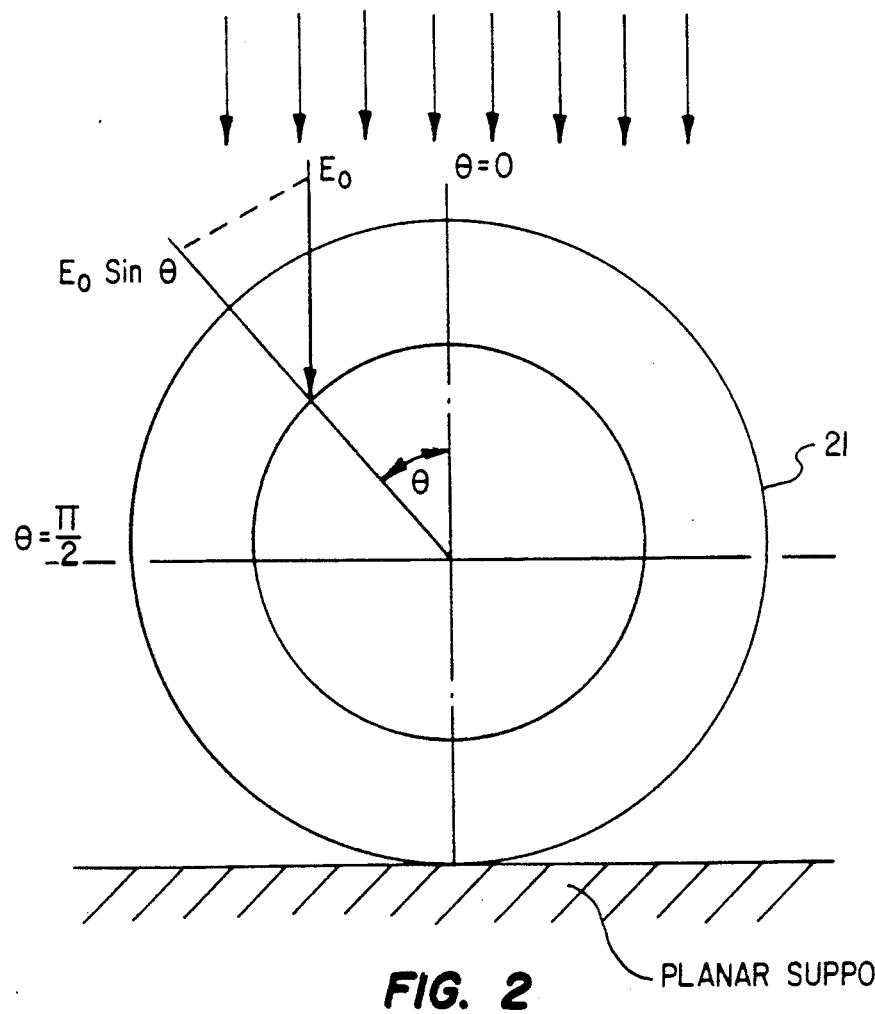
FIG. 2 is an enlarged cross-sectional view of the flexible transparent plastic tube of FIG. 1.

FIG. 2 shows the enlarged cross-sectional view of the flow tube, 21, sitting on a planar support with the incident light, $I_o$, coming in along the direction as shown by arrows.

The corresponding average fluence $<E>$ over the hemicylindrical surface of flow tube is obtained by the integral:

$$<E> \ = \ \frac{2 E_o \int_0^{\pi/2} \sin\theta d\theta}{2 \int_0^{\pi/2} d\theta} \ = \ \left(\frac{2}{\pi}\right) E_o$$

where ($E_o \sin\theta$) is the component of $E_o$ perpendicular to the hemicylindrical surface at the point defined by the angle $\theta$ between the radius vector to the point and the direction antiparallel to the direction of the incident light.

Figure 3:
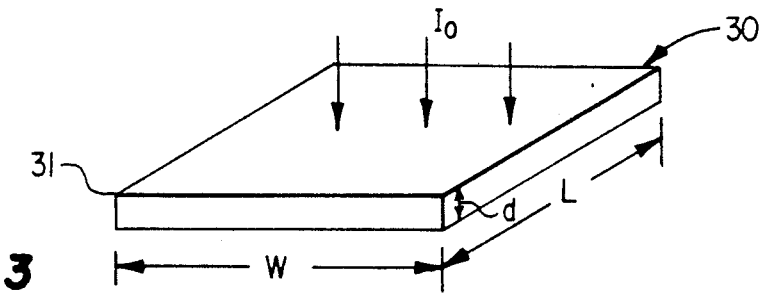
FIG. 3 is a perspective view of the irradiation cell being irradiated from the top of the cell.
Figure 3A:
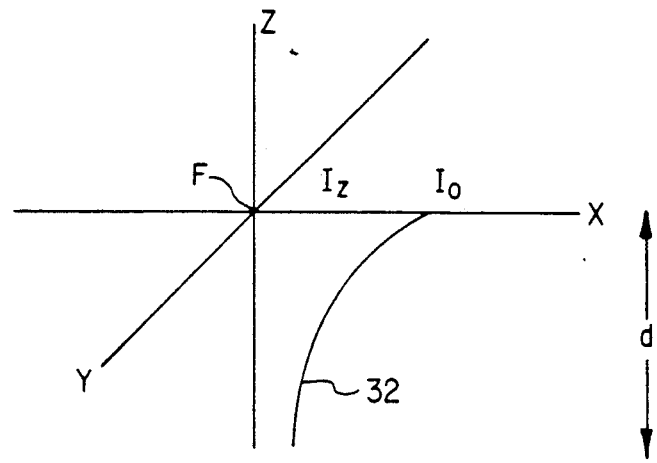

Although useful in demonstrating the efficacy of dihematoporphyrin ether (DHE) based photodynamical killing of infectious pathogens in blood or other body fluid, the embodiment described above is limited in at least two ways. Firstly, throughput rate is severely limited. Secondly, due to variation in irradiance with angle $\theta$ and due to light absorption and scattering, light exposure at various depths below the illuminated cylindrical surface of the flowing fluid volume element varies with positions along the diameter of the tube. Uniformity of light intensity with depth, and hence, calculation and control of dosimetry, would be improved if the blood or other body fluid would flow as a plane layer of uniform thickness, d, which is exaggerated in the drawing, with the uniform surface illumination as shown in FIG. 3. When it is the body fluids that are to be treated photochemically, the cell 30 would function as a flow cell to direct the flow of body fluids. If, on the other hand, it is the thin layer of body tissue to be subjected to photochemical treatment, the cell would serve to hold the suspension of body tissue in a physiologically suitable saline solution.

Still referring to FIG. 3, the uniform width of the irradiation cell 30 is denoted by W, while the uniform length of the cell is L. In this scheme, the incident light $I_o$ and the falloff of light intensity $I_z$ with depth along Z axis is everywhere uniform on any plane of constant depth from the irradiated surfaces. Additionally, flow rate within such a layer with much larger cross-sectional area than the previously used tubing is considerably enhanced.

FIG. 3-a shows the decrease of the intensity of unidirectional irradiation as the irradiating light travels along the depth, d, of the irradiation cell 30, as depicted in FIG. 3. The geometry of the irradiation is graphically illustrated as a three-dimensional rectangular coordinate system (X, Y, Z). The two horizontal axes are X and Y, while the vertical axis is Z. The depth, d, of the irradiation cell 30 is defined by the Z axis; the width, W, of the irradiation cell 30 is defined by X axis; and the length, L, of the irradiation cell 30 is defined by Y axis. The origin F represents point 31 at the upper left hand corner of the irradiation cell 30.

Referring still to FIG. 3-a, the Z component, $I_z$, of the irradiating light $I_o$, as represented by line 32, decreases in intensity as the light travels through the thickness d of the cell 30. The decrease in intensity is a function of the distance of the path travelled by the irradiation, as is shown by line 32 which approaches zero as the distance travelled by light along the thickness d increases.

Figure 4:
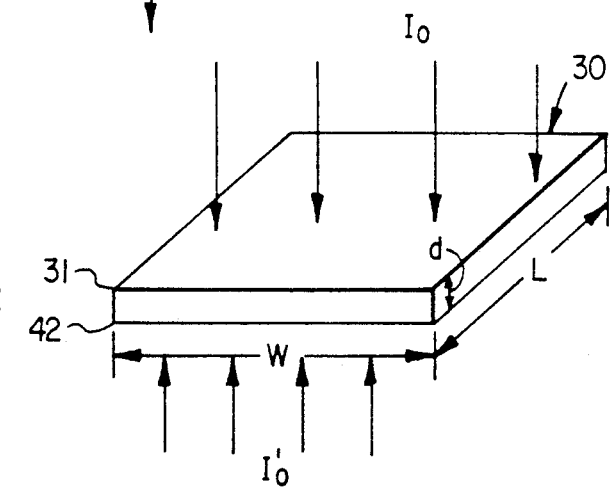
FIG. 4 is a perspective view of the irradiation cell being irradiated from both the top and the bottom of the cell.
Figure 4A:
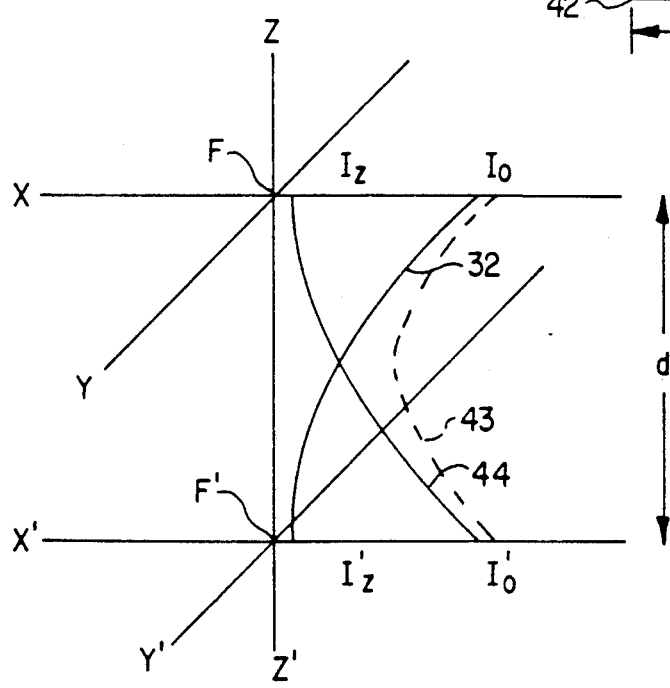

FIG. 4 shows the irradiation cell 30 being irradiated from both vertical directions. The irradiation cell 30 could either be a flow cell directing the flow of body fluids or a cell housing a suspension of body tissues in a physiologically acceptable saline solution. The uniform irradiation from the top of the cell assembly, as shown by arrows pointing downward, along the width d, is represented by $I_o$; while the uniform irradiation from the bottom of the cell assembly, as shown by arrows pointing upward along the width d, is represented by $I_{o'}$. The uniform thickness of the irradiation cell 30 is represented by d and is exaggerated in the diagram. The width of the cell 30 is represented by W, while the length of the cell 30 is represented by L. Both L and W are again of uniform dimensions in this embodiment.

FIG. 4-a graphically depicts the geometry of the double irradiations as two three-dimensional rectangular coordinate systems, (X, Y, Z) and (X', Y', Z'). The four horizontal axes are X, Y, X', and Y'. The two vertical axes are Z and Z'. The depth d of the irradiation cell 30 is represented by the two vertical axes, Z and Z'; the width W of irradiation cell 30 is represented by horizontal axes X and X'; and the length L of the irradiation cell 30 is represented by horizontal axes Y and Y'. The origins F and F' represent points 31 and 42, respectively, in FIG. 4.

As is shown in FIG. 3-a, the Z component, $I_z$, of the irradiation $I_o$ decreases in intensity as the light travels through the thickness d of the irradiation cell 30. This decrease in intensity is depicted by line 32 which approaches zero as the distance travelled by light along the thickness d increases.

Likewise, the Z' component, $I_{z'}$, of the irradiation $I_{o'}$ decreases in intensity as the light travels through the thickness d of the irradiation cell 30. The change in intensity is depicted by line 44 which approaches zero as the distance travelled by light along the thickness d increases. Still referring to FIG. 4-a, when the irradiation cell 30 is irradiated from both directions by uniform light beams $I_o$ and $I_{o'}$, the total intensity of Z component obtained is $I(z+z')$ which is equal to the summation of $I_z$ and $I_{z'}$ as represented by the broken line 43. The intensity of light represented by line 43 is, at all times, greater than the intensity represented by either line 32 or line 44 alone. Consequently, when the irradiation cell 30 is irradiated from two opposite directions, the resultant light intensity obtained in the cell 30 is greater than the intensity obtained when the cell 30 had been irradiated from one direction only.

Figure 5:
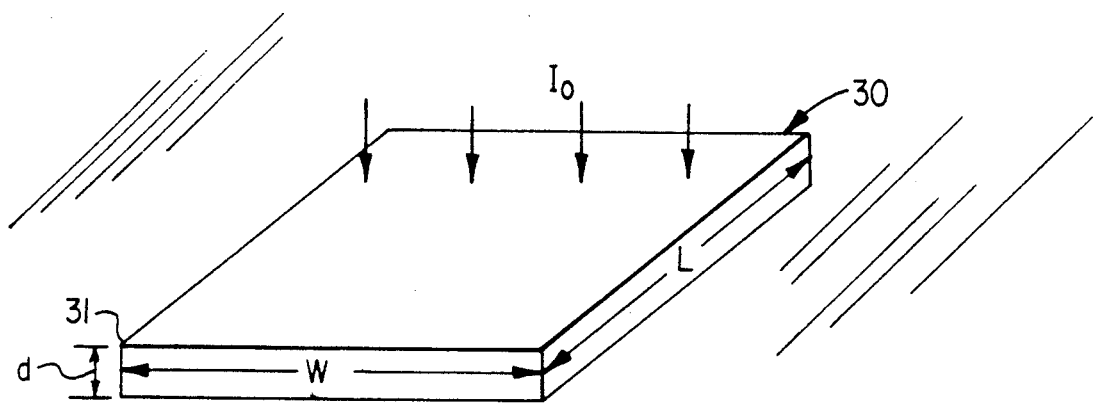
FIG. 5 is a perspective view of the irradiation cell being supported on the bottom by a reflecting mirror surface while the cell is being irradiated from the top of the cell.
Figure 5A:
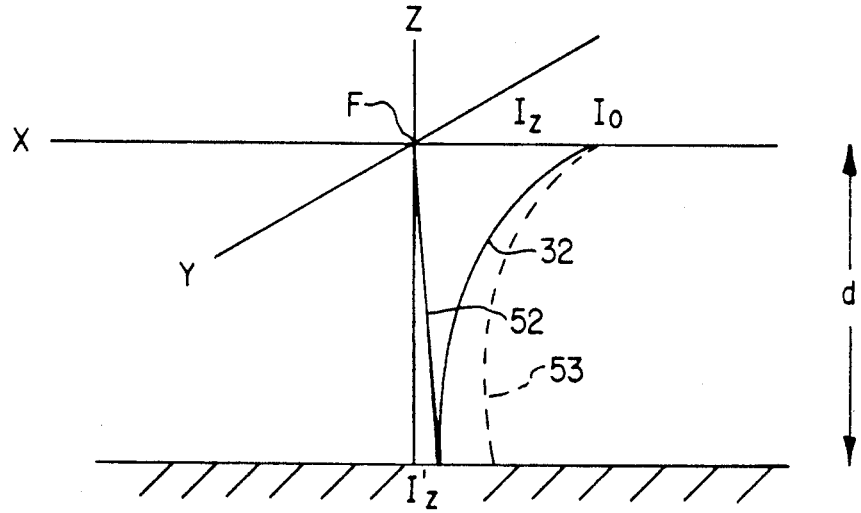

FIG. 5 illustrates the irradiation cell 30 being supported by a reflecting mirror surface while the cell is being irradiated by a uniform light beam $I_o$ from the opposite direction as shown by the arrows. As in FIG. 4, the irradiation cell 30 could either be a flow cell directing the flow of body fluids or a cell housing a suspension of body tissues in a physiologically acceptable saline solution. The uniform thickness of the irradiation cell 30 is represented by d and is exaggerated in the diagram. W represents the uniform width of the irradiation cell 30, while L represents the uniform length of the irradiation cell 30.

FIG. 5-a graphically depicts the geometry of the irradiation and its reflection from the supporting reflecting mirror as a three-dimensional rectangular coordinate system (X, Y, Z). The two horizontal axes are X and Y, while the vertical axis is Z. The depth, d, of the irradiation cell 30 is defined by Z axis; the width, W, of the irradiation cell 30 is defined by X axis; and the length, L, of the irradiation cell 30 is defined by Y axis. The origin F represents point 31 of the irradiation cell 30.

FIG. 5-a shows the Z component, $I_z$, of the irradiation $I_o$ decreases in intensity as the light travels through the thickness d of the irradiation cell 30. This decrease in intensity is depicted by line 32 which approaches zero as the distance travelled by light along the thickness d increases.

The Z component of this reflected light, $I_{z''}$, approaches zero as the reflection travels through the thickness d of the irradiation cell 30.

Still referring to FIG. 5-a, with the introduction of the reflecting mirror as a support for the irradiation cell 30, however, the total intensity along Z component obtained in $I(z+z'')$ which is equal to the summation of $I_z$ and $I_{z''}$ as represented by the broken line 53. The intensity of light represented by line 53 is greater than the intensity represented by either line 32 or line 52 alone. Consequently, the introduction of a reflecting mirror also enhances the light intensity obtained in the irradiation cell 30.

Figure 6:
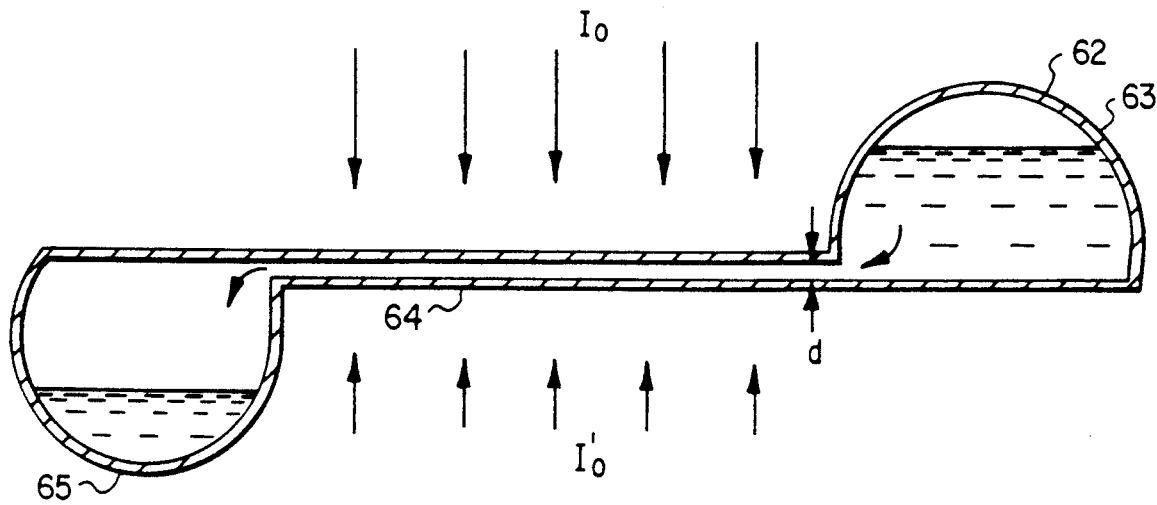
FIG. 6 is a longitudinal sectional view of another embodiment of the flow cell.

FIG. 6 shows the longitudinal sectional view of another embodiment of the flow cell. The flowing layer of blood or body fluid is confined within a transparent, thin walled, (62), flexible, flat tubular volume, 64, connecting a collection bag 63, and a receptacle bag 65. After the body fluid flows from the collection bag 63 through the flat tubular space 64 where the body fluid is illuminated, the body fluid is received and ultimately stored in the receptacle bag 65. Representative dimensions for the flowing layer in the illuminated zone are width = 5 cm; length = 40 cm; thickness d = 0.05 cm. For this configuration, representative treatment conditions include a total incident light intensity of $1.04 \times 10^{-1}$ w/cm$^2$ at $630 \pm 5$ nm wavelength divided equally over both lateral $40 \times 5$ cm surfaces ($5.02 \times 10^{-2}$ w/cm$^2$ to each) combined with a flow rate of about 24.96 cm$^3$/min. This combination led to a total incident fluence over the two surfaces of an elemental volume of 5 J/cm$^2$. This light dosage with a Photofrin II ™ concentration of $2.5 \times 10^{-6}$ gm/cm$^3$ has been demonstrated to effectively kill envelope viruses and other infectious pathogens.

Figure 7:
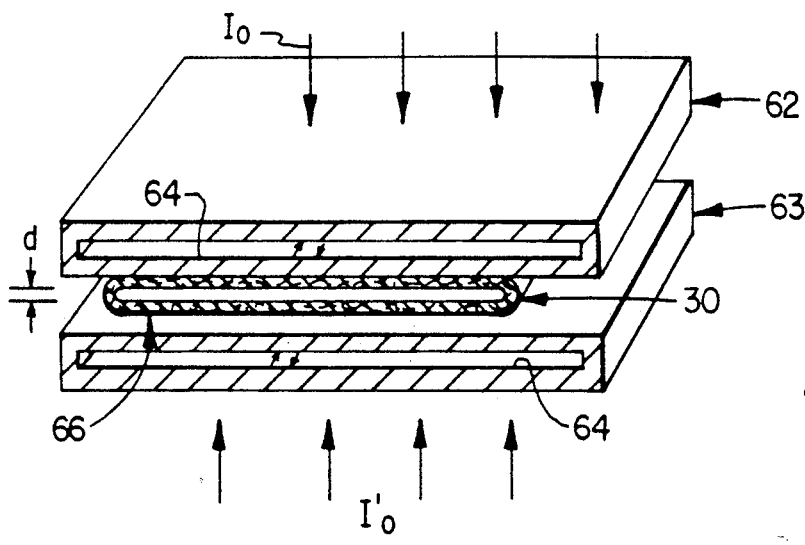
FIG. 7 shows a perspective view of the irradiation cell sandwiched between two transparent flat platens while the assembly is being irradiated from two opposite directions, top and bottom, of the cell.

In order to maintain uniform thickness, d, in the irradiation cell 30, the cell 30 can be constrained between two transparent flat platens, 62 and 63, held apart at the correct distance with a spacer as shown in FIG. 7. These platens can be hollow to allow the circulation of a heat exchange medium, 64, to cool the irradiated body tissue, either as a flowing body fluid or as a suspension of body tissue, in a physiologically acceptable saline solution. In this way, deleterious photothermal effects such as red cell lysis potentially resulting from absorption of incident light by hemoglobin can be minimized while maintaining a high incident light fluence. The whole system can be illuminated with light sources entering the system from two opposite directions, as depicted by $I_o$ and $I_{o'}$. Alternatively, the surface of one of the flat platens can be made up of reflective mirror to reflect the single unidirectional irradiation coming in from the opposite direction.

Illumination from two opposite directions, instead of just one, helps to overcome effects of light intensity falling off with penetration depth into the flowing body fluid due to light absorption and scattering (FIG. 4-a). Suitable light sources for illumination include lamp and laser sources. Especially suitable is a xenon, quartz halogen or metal vapor lamp with output energy containing the wavelength range of $630 \pm 5$ nm. These lamps are available in long straight small diameter tubular shape; hence they can be easily arranged in a coparallel fashion in two planes which are parallel to the flowing blood layer surfaces to illuminate these surfaces (FIG. 8).

Figure 8:
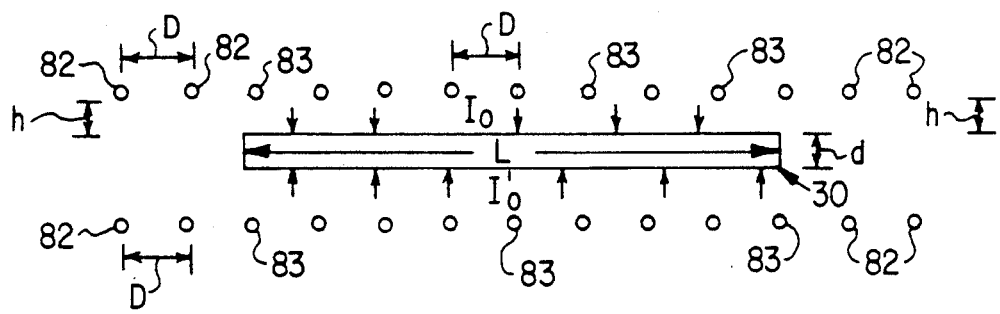
FIG. 8 shows the longitudinal sectional view of the irradiation cell surrounded on the top and bottom with two arrays of tubular lamps which are depicted cross-sectionally as small circles.

FIG. 8 shows the longitudinal sectional view of the irradiation cell 30 sandwiched between two arrays of long and tubular lamps, 82 and 83, to give a uniform irradiation over both surfaces of the flow cell 30 along the length L. The cross-sectional view of the light sources, 82 and 83, are drawn as small circles in the picture. The irradiation cell 30 could either be a flow cell directing the flow of body fluids or a cell housing a suspension of body tissues in a physiologically acceptable saline solution.

These long tubular lamps, 82 and 83, each parallel to the other, were arranged with their length parallel to the width of the cell 30. When the distance D between the adjacent lamps was equal to the distance h between the plane containing the array of lamps and the illuminated surface of the irradiation cell 30, the mean variation in light flux along the layer length L of the irradiation cell 30 was less than approximately 2.5% provided the lamp array extends beyond the length of the irradiation cell 30 by at least 2 additional lamps 82 at both ends. The result is graphically depicted in FIG. 9 as a two-dimensional coordinate system (X, Y).

Figure 9:
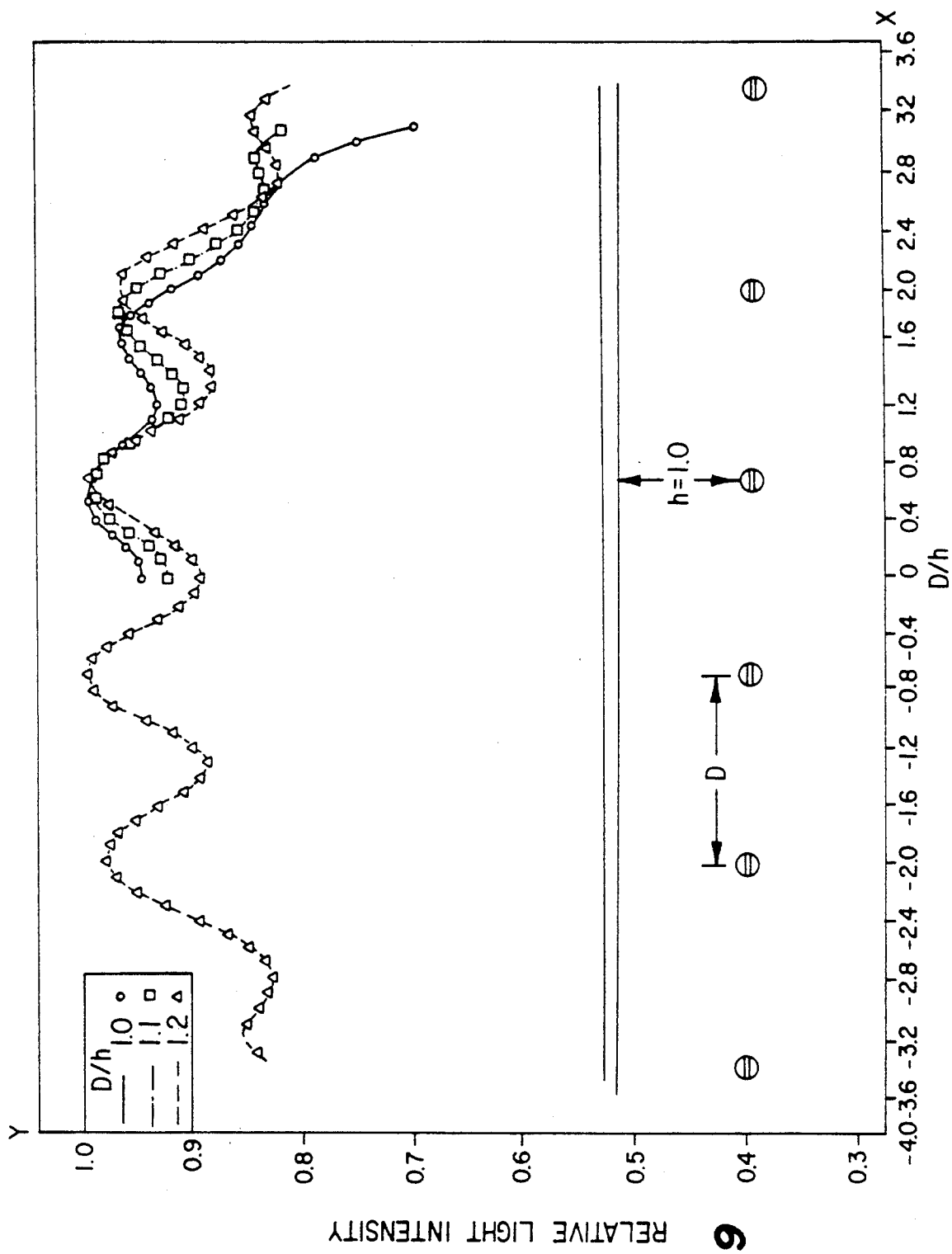
FIG. 9 is a plot of normalized relative light intensity vs. the ratio of distance D with respect to distance h. Distance D is the spacing between two adjacent lamps, while distance h is the separation between the plane containing the array of lamps and the illuminated surface of the irradiation cell.

In FIG. 9, the horizontal axis denotes the ratio $D/h$. D is the spacing between two adjacent lamps; while h is the separation between the plane containing the array of lamps and the illuminated surface of the irradiation cell.

The vertical Y axis denotes the relative light intensity. In this particular graph, the distance h was normalized to a value of 1. The lamps are parallel to each other and are arranged in a plane parallel but along the width of the irradiation cell. A total of six lamps, equally spaced from one another at a distance D, were used. The width of the tubular lamp was roughly one-tenth the value of h. Relative to distance h, which was normalized to a value of 1, the separation between two adjacent tubular lamps was 1 (denoted by small circles in the graph), 1.1 (denoted by small squares in the graph) or 1.2 (denoted by small triangles in the graph). This relative separation was plotted against the variation in light flux in FIG. 9. The solid line, formed by joining small circles, represents the variation in light flux when the tubular lamps were separated from one another by a distance equal to h. The solid line shows that the mean variation in light flux among the four internal lamps, hence along the layer length of the flow cell, was less than 2.5%.

Figure 10:
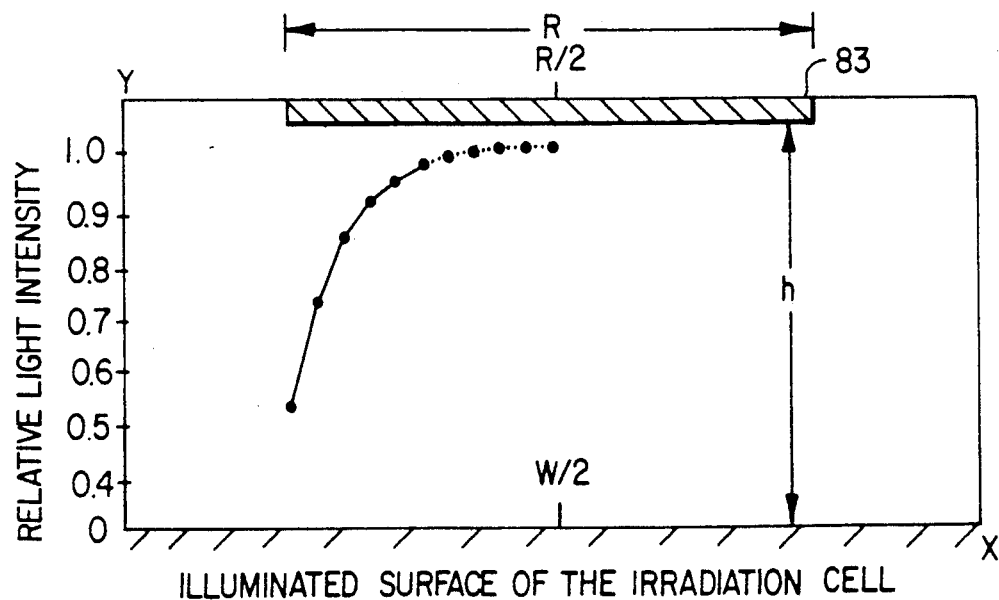
FIG. 10 is a plot of normalized relative light intensity along the length of the tubular lamp. The longitudinal sectional view of the lamp is shown on top of the diagram.

FIG. 10 is a plot of relative light intensity along the length R of the tubular lamp 83. The vertical Y axis of the two-dimensional rectangular coordinate represents the relative light intensity with the maximum intensity arbitrarily assigned a unit valve of 1. The horizontal X axis represents the illuminated surface of the irradiation cell which was parallel to the tubular lamp 83. Again the distance between the plane containing the lamps and the surface of the irradiation cell is h. It can be seen from FIG. 10 that the light intensity was at its maximum, arbitrarily assigned a unit value of 1, around the midpoint R/2 along the length R of the tubular lamp 83. The light intensity gradually fell off toward the two terminals of the tubular lamp 83.

Thus, when the length L of each tubular lamp was twice the width W of the irradiation cell and placed with its mid-point L/2 above the midpoint W/2 of the layer width, the mean variation in light intensity with width of the irradiation cell was less than 1.6%.

In order to achieve an essentially uniform total irradiance of $1.04 \times 10^{-1}$ w/cm$^2$ over the two surfaces of the irradiation cell, $5.02 \times 10^{-2}$ w/cm$^2$ must be provided to each side. When an area with the width of 10 cm and the length of 40 cm was irradiated with 4 lamps spaced at 2 cm apart and a lamp length of 10 cm, 24.10 watts output per lamp bank was obtained. Using a total of 24 lamps per surface resulted in a requirement of 1.04 watts output lamp emitting the energy in the range of 630±5 nm. This arrangement gave 10.04 watts per surface incident on the flowing body fluid in the flow cell. Dichroic lamp coatings and/or platen coatings as well as infra-red absorbing filters could be used to ensure no thermal damage to optics, suspended body tissue, or flowing body fluid would take place.

It should be emphasized that all the procedures described above are to be carried out in a closed system to prevent the exposure of the body tissues to the unsterile environment.

Figure 11:
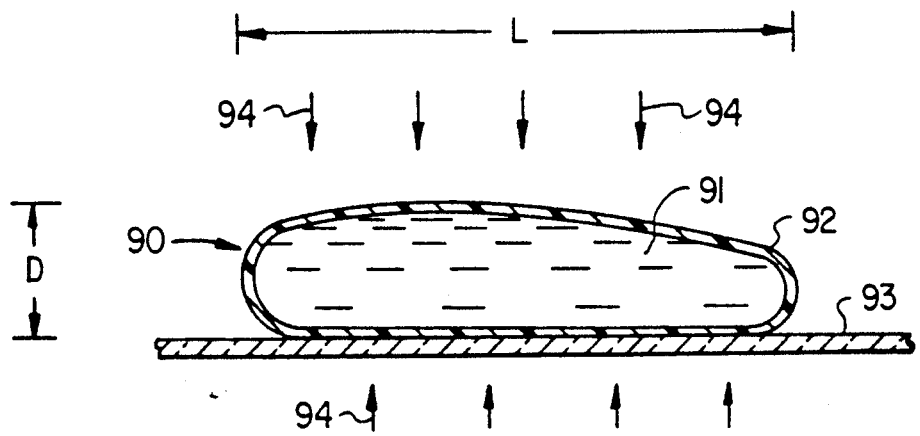
FIG. 11 is a cross-sectional view of a schematic diagram of a closed container in the form of a flexible transparent plastic bag which is partially filled by body fluids and kept static.

Referring now to FIG. 11, there is shown a schematic closed container in the form of a flexible and transparent plastic blood bag 90. When containing a typical volume of contaminated or infected body fluids 91 after being added an appropriate concentration of a photoactive compound, the bag 90 has a width W, a length L, and a thickness D, such that $W \sim L \gg D$. Typically, it is 12 cm × 12 cm × 2 cm. The bag 90 is filled with contaminated body fluids 91 to a volume that is a fraction of the maximum volume which can be held by the bag 90. Thus, the bag 90 is not filled to its capacity. No additional liquid or gas is present within the partially filled bag 90, however.

By placing the bag 90 on a transparent support platform 93, the bag 90 with the contaminated body fluids 91 can be illuminated uniformly over the lateral bag area with light with an appropriate wavelength from both the top and bottom as indicated by arrows 94. The effectiveness of the photosensitization of the photoactive compound and the decrease of infectivity of the contaminants in the infected body fluids 91 can be monitored by control infectivity assays.

Figure 12:
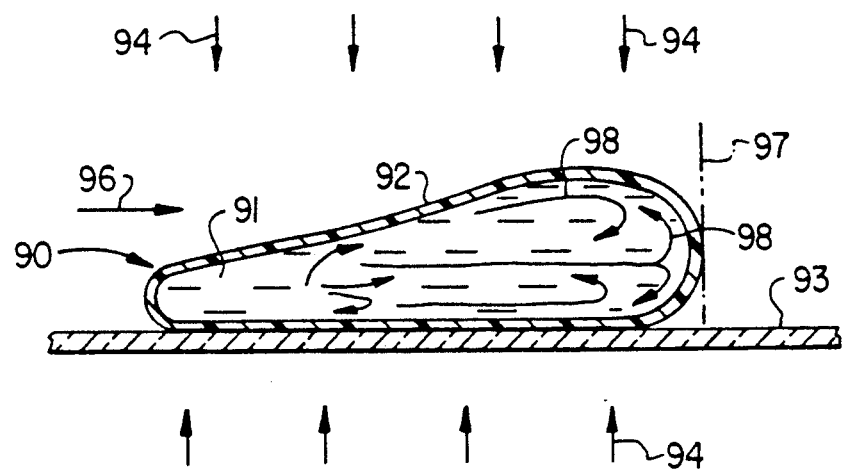
FIG. 12 is a schematic diagram of the plastic bag of FIG. 11 moving to the right.

Referring to FIG. 12, bag 90 is shown being moved or pushed to the right, along and parallel to, the direction of length L as indicated by arrow 96. The right hand external sidewall of the bag 90 stops at position 97. In this way, the mixing motions of internal fluids are augmented in magnitude by inertial effects of the fluid deceleration upon its encountering the internal bag walls 92 during agitation. The movement of the bag 90 causes agitation and cyclically opposing translational mixing motions of the contaminated body fluids 91 as indicated by arrows 98. The uniformity of fluid mixing can be substantially enhanced by also moving the bag 90 in cyclically opposing or reciprocating translational motions in a direction parallel to the width W (not shown) or parallel to the thickness D. Moreover, a movable agitating object, such as a bar or a ball, placed inside the bag 90 will also enhance the mixing. By placing the bag 90 during motion on a transparent support platform 93, the bag 90 with its infected body fluids 91 containing an appropriate concentration of a photoactive compound can be uniformly illuminated by light of appropriate wavelength from both the top and bottom directions as shown by arrows 94.

Figure 13:
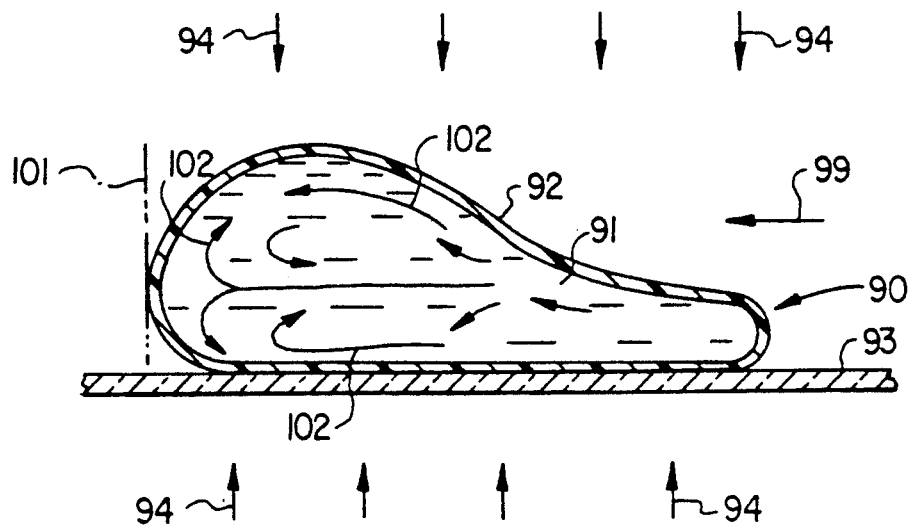
FIG. 13 is a schematic diagram of the plastic bag of FIG. 11 moving to the left.

Referring to FIG. 13, it is shown that the bag 90 is being moved or pushed to the left, along and parallel to, the direction of length L as indicated by arrow 99. The external left hand side of the bag 90 stops at position 101. Arrows 102 indicate the mixing motions of the contaminated or infected body fluids 91.

Figure 14:
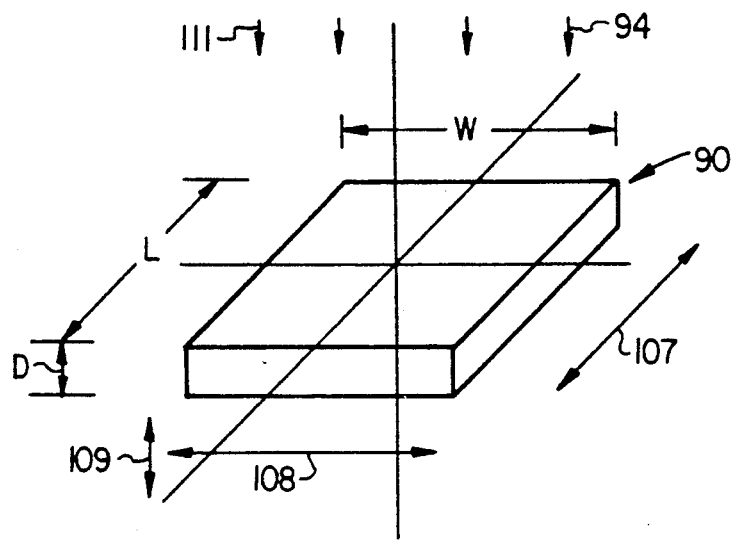
FIG. 14 is a perspective view of a schematic diagram of a transparent closed container showing the possible directions of reciprocating translational motions.

FIG. 14 shows the possible directions of reciprocatory translation motions of a closed transparent container 90 having contaminated body fluids and a photoactive compound inside. Arrow 107 shows the direction of reciprocating movement along and parallel to the length L. Arrow 108 shows the directions of reciprocatory movement along and parallel to the width W. Arrow 109 shows the directions of reciprocatory movement along and parallel to the thickness D. The container with the infected body fluids inside can be uniformly illuminated by light from both the top and the bottom, as shown by arrows 94.

Figure 15:
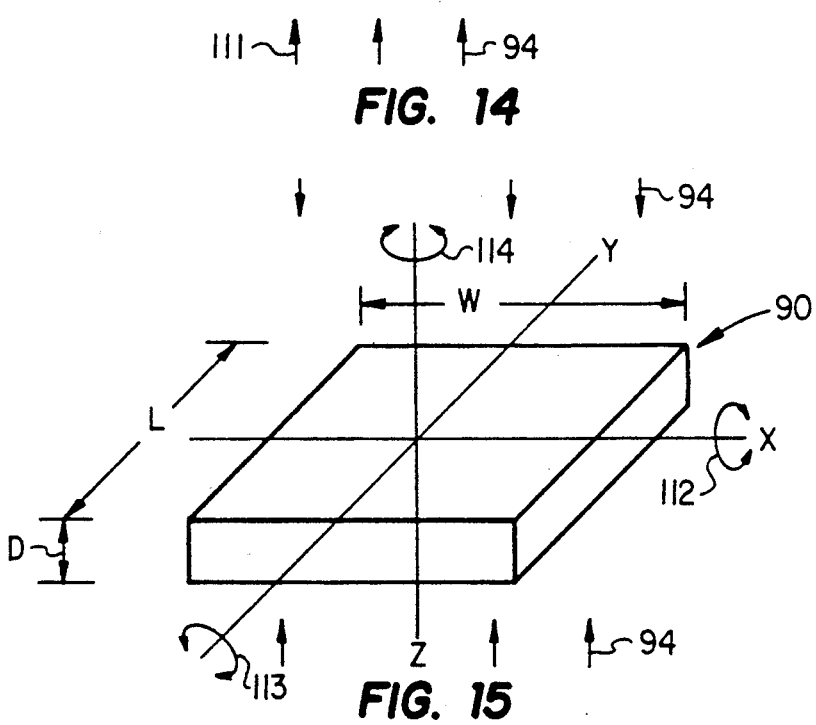
FIG. 15 is a perspective view of a schematic diagram of a transparent closed container showing the possible directions of reciprocatory rotational motions.

FIG. 15 shows the possible directions of reciprocatory rotational motions of the closed container 90 having infected body fluids and a photoactive compound inside. Arrow 112 shows the directions of reciprocatory rotational movement along the X-axis of the three-dimensional rectangular coordinate system. Arrows 113 and 114 show the directions of reciprocatory rotational movement along the Y-axis and Z-axis, respectively, of the coordinate system.

Figure 16:
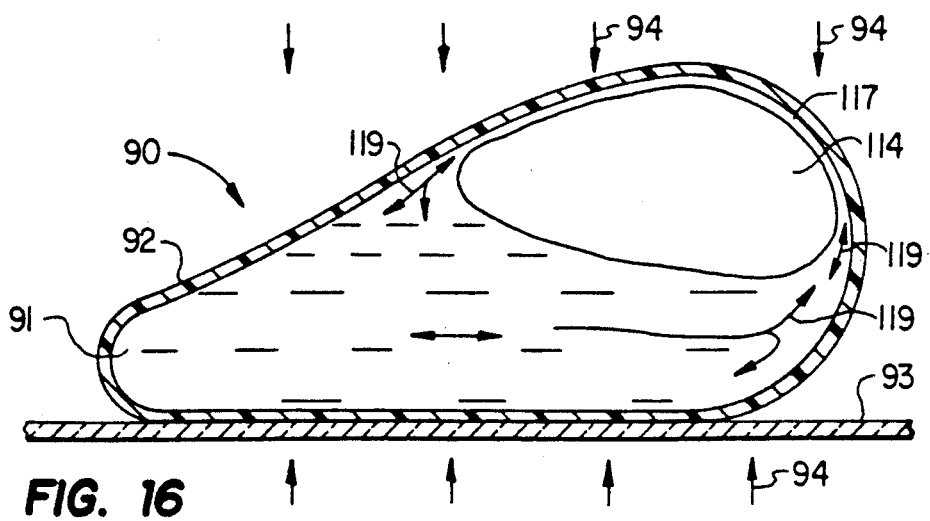
FIG. 16 is a cross-sectional view of a schematic diagram of a closed container in the form of a flexible transparent bag which is partially filled with contaminated body fluids and has an air bubble.

Referring now to FIG. 16, there is shown a cross-sectional view of a schematic diagram of a closed container in the form of a flexible transparent bag 90. The bag 90 is partially filled with infected or contaminated body fluids 91 containing an appropriate concentration of a photoactive compound. A chemically inert and sterilized gas, such as air, is introduced into the bag to create an air bubble 124 on the top. With the addition of an air bubble 114, the agitation of the bag 90 will create an additional result of internal fluid mixing. This result is brought about by the formation of an optically thin layer or film 117 of body fluids at the interface of bag 90 and bubble 114. Arrows 119 indicate motions of body fluids 91 in the bag 90. This film 117 is repetitively renewed from the rest of the body fluid volume 91 during agitation or mixing. With the optimum relative volume of bubble and liquid, essentially the entire lateral surface of area L×W will be covered with such a film. Light exposure is continued until control infectivity assays demonstrate the required decrease in infectivity.

In order to more fully describe the present invention the following examples are set forth. However, it is to be understood that the examples are for illustrative purposes and are not to be construed as limiting the scope of the invention as defined in the appended claims.

EXAMPLES

Photo-Irradiation of Human Blood

Photo-irradiation of human blood was performed in a prototype instrument as described in FIG. 1. The human blood was pumped using a syringe pump through narrow bore plastic tubing attached to a small glass plate with epoxy adhesive. The tubing followed a serpentine route across the plate. The blood was pumped through the tubing at a rate of 22.6 microliters per minute. Normal blood samples were divided into 4 separate aliquots. Aliquot 1 was pumped through the cuvette following pretreatment with Photofrin II TM (from Johnson and Johnson; containing approximately 90% of pure dihematoporphyrin ether (DHE)) and without photo-irradiation. Aliquot 2 was treated in an identical fashion except that it was photo-irradiated as it flowed through the cuvet. Aliquot 3 was incubated with Photofrin II TM for 25 minutes then passed through the flow cell without photo-irradiation. Aliquot 4 was incubated for 25 min. with Photofrin II TM then pumped through the flow cell as before except the aliquot was photo-irradiated. Thus, aliquots 1 through 3 are appropriate controls for aliquot 4.

Blood samples were obtained from four normal healthy individuals, (LM, JEL, LH, RB). One blood sample (HS) was pretreated with *Herpes simplex* virus type I prior to irradiation while two samples (BL and BD) were from patients suffering from acquired immune deficiency syndrome (AIDS).

Samples obtained from patients found positive to the human immunodeficiency virus (HIV) antibody were divided into two aliquots and treated like aliquots 1 and 4 described above.

Fibrinogen assays were performed according to the procedure published by K. Jacobson (Scand. J. Clin. Lab. Med. 7:7, 1955), using commercial reagents (American Dade). Osmotic fragility was performed using commercial reagents according to the method described by Dacie and Lewis (J. V. Dacie & S. M. Lewis, Practical Haematology Churchill Livingston, 1975). Sugar water lysis test was performed according to the method described by Dacie and Lewis (Practical Haematology). Prothrombin time was measured using commercial reagents (American Dade) using the automated coagulation instrument MLA700 (Medical Laboratory Automation). The activated partial thromboplastin time (APTT) was performed using commercially available reagents (American Dade) according to methods described by that company using the MLA700 coagulation instrument. Electrolytes sodium potassium calcium were measured using the Nova 6 electrolyte analyzer which employs ion specific electrodes according to methods established by the manufacturer. Glucose was measured in plasma samples using the Beckman Glucose Analyser Model 2 according to procedures recommended by Beckman Instruments Corp. Blood counts were measured using the fully automated machine Coulter S PLUS IV (Coulter Electronics). Differential counts were performed manually using a blood smear prepared by the wedge technique on a glass slide and the blood was then stained with Wright's Stain. Oxygen dissociation was performed on the Aminco Hem-O-Scan according to methods described by that manufacturer. Serum protein electrophoresis was performed according to the method described by Helena Laboratories on equipment manufactured by them. All the above methods are in routine use in these laboratories. The results are tabulated in Tables II through IV, followed by listings of abbreviations used in the Tables.

TABLE II

RESULTS: Human Blood From Normal. Healthy Volunteers

| Donor | LM | LM | JEL | JEL | JEL | JEL | |
|---|---|---|---|---|---|---|---|
| Date | 12/28 | 12/28 | 1/5 | 1/5 | 1/5 | 1/5 | |
| Time | 09:00 | 13:00 | 08:35 | 08:35 | 24:00 | 24:00 | hrs. |
| Light | yes | yes | no | yes | no | yes | |
| Photofrin | 0 | 2.5 | 0 | 0 | 2.5 | 2.5 | ug/mL. |
| Sodium | 152.0 | 138.1 | 145.0 | 159.5 | 156.8 | 158.3 | mM. |
| Potassium | 4.07 | 7.36 | 18.62 | 3.69 | 6.25 | 3.54 | mM. |
| Calcium | .06 | 0.05 | 0.06 | 0.06 | 0.07 | 0.07 | mM. |
| Glucose | 153 | 89 | 72 | 88 | 79 | 83 | mg/dL. |
| | 158 | 92 | 71 | 87 | 79 | 83 | mg/dL. |
| Osmotic Frag. | | | | | | | |
| Begin: | 0.46 | 0.46 | 0.46 | 0.46 | 0.46 | 0.46 | % |
| 50%: | 0.40 | 0.40 | 0.44 | 0.44 | 0.44 | 0.44 | % |
| complete: | 0.34 | 0.30 | 0.34 | 0.34 | 0.34 | 0.34 | % |
| Sugar Wat. lys | 0.100 | 0.260 | 0.645 | 0.000 | 1.095 | .099 | O.D. 540 |
| Fibrinogen: | 327 | 227 | 325 | 325 | 341 | 298 | mg/dl. |
| PT: | ONS | 13.9 | 11.3 | 11.6 | 12.0 | 13.1 | secs. |
| APTT | 35.5 | 37.0 | 27.8 | 26.2 | 29.4 | 29.3 | secs. |
| Factor Def. Scn. | | | | | | | |
| Factor II | neg. | neg. | neg. | neg. | neg. | neg. | |
| Factor V | neg. | neg. | neg. | neg. | neg. | neg. | |
| Factor VII | neg. | neg. | neg. | neg. | neg. | neg. | |

TABLE II-continued
RESULTS: Human Blood From Normal, Healthy Volunteers

| | | | | | | | |
|---|---|---|---|---|---|---|---|
| Factor X | neg. | neg. | neg. | neg. | neg. | neg. | |
| Factor VIII | neg. | neg. | neg. | neg. | neg. | neg. | |
| IX | neg. | neg. | neg. | neg. | neg. | neg. | |
| XI | neg. | neg. | neg. | neg. | neg. | neg. | |
| XII | neg. | neg. | neg. | neg. | neg. | neg. | |
| CBC... | | | | | | | |
| WBC | 6.5 | 6.4 | 7.0 | 8.1 | 3.3 | 3.8 | Thous. |
| RBC | 4.53 | 4.51 | 4.45 | 2.37 | 4.83 | 4.77 | Mill. |
| HGB | 15.1 | 14.9 | 13.1 | 7.35 | 14.5 | 14.1 | g/dL. |
| HCT | 43.2 | 45.2 | 47.4 | 21.6 | 43.9 | 42.4 | % |
| MCV | 102 | 100.3 | 107.0 | 88.0 | 91.0 | 91.0 | fl. |
| MCH | 33.3 | 33.1 | 29.5 | 30.4 | 30.0 | 29.8 | pg. |
| MCHC | 32.7 | 33.0 | 27.6 | 34.1 | 32.9 | 33.5 | g/dL. |
| RDW | 13.4 | 12.5 | 23.0 | 9.8 | 14.1 | 11.8 | % |
| Platelets | 145 | 151 | 127.0 | 235 | 85 | 88 | Thous. |
| Differential | | | | | | | |
| Total polys | 70 | 57 | 69 | 61 | 66 | 70 | % |
| segs | 68 | 57 | 69 | 61 | 65 | 70 | % |
| bands | 2 | 0 | 0 | 0 | 1 | 0 | % |
| lymphs. | 25 | 38 | 25 | 29 | 30 | 26 | % |
| monos. | 4 | 4 | 5 | 7 | 3 | 1 | % |
| eosin. | 1 | 1 | 1 | 3 | 0 | 1 | % |
| baso | 0 | 0 | 0 | 0 | 1 | 0 | % |
| Direct Coombs | neg. | +/− IGg + | neg. | neg. | neg. | neg. | |
| Serum Elec | NA | NA | | | | | |
| Albumin | NA | NA | 16.72 | 54.83 | 39.18 | 52.99 | % |
| alpha 1-Glob | NA | NA | 3.01 | 5.68 | 4.99 | 5.60 | % |
| alpha 2-Glob | NA | NA | 5.17 | 10.55 | 7.88 | 10.72 | % |
| beta - Glob | NA | NA | 62.39 | 12.00 | 31.92 | 13.43 | % |
| gama - Glob | NA | NA | 12.71 | 16.95 | 16.02 | 17.26 | % |
| O2 Dissociatn p50 | | | 29 | | 29 | 29 | mmHg |
| Comments | | | *1 | *2 | *1 | | |

| | | | | | | | |
|---|---|---|---|---|---|---|---|
| Donor | LH | LH | LH | LH | RB | RB | |
| Date | 1/6/87 | 1/6/87 | 1/6/87 | 1/6/87 | 1/7/87 | 1/7/87 | |
| Time | 0847 | 0847 | 1130 | 1130 | 0850 | 0850 | hrs. |
| Light | no | yes | no | yes | no | yes | |
| Photofrin | 0 | 0 | 2.5 | 2.5 | 0 | 0 | ug/mL. |
| Sodium | 157.5 | 158.4 | 155.7 | 155.3 | 155.5 | 154.5 | mM. |
| Potassium | 3.37 | 3.26 | 3.34 | 3.37 | 3.44 | 3.37 | mM. |
| Calcium | 0.06 | 0.06 | 0.06 | 0.06 | 0.06 | 0.06 | mM. |
| Glucose | 66 | 64 | 65 | 61 | 81 | 80 | mg/dL. |
| | 65 | 63 | 65 | 62 | 81 | 77 | mg/dL. |
| Osmotic Frag. | | | | | | | |
| Begin: | 0.50 | 0.05 | 0.50 | 0.50 | 0.46 | 0.46 | % |
| 50%: | 0.46 | 0.46 | 0.46 | 0.46 | 0.44 | 0.44 | % |
| complete: | 0.34 | 0.34 | 0.30 | 0.30 | 0.30 | 0.30 | % |
| Sugar Wat. lys | 0.003 | 0.019 | 0.000 | 0.000 | 0.000 | 0.000 | change in OD @ 540 nm |
| Fibrinogen: | 377 | 320 | 358 | 302 | 286 | 298 | mg/dl. |
| PT: | 10.9 | QNS | 11.5 | 12.5 | 11.9 | 11.9 | secs. |
| APTT | 24.0 | 25.0 | 25.0 | 27.0 | 34.7 | 36.5 | secs. |
| Factor Def. Scn. | | | | | | | |
| Factor II | neg. | neg. | neg. | neg. | neg. | neg. | |
| Factor V | neg. | neg. | neg. | neg. | neg. | neg. | |
| Factor VII | neg. | neg. | neg. | neg. | neg. | neg. | |
| Factor X | neg. | neg. | neg. | neg. | neg. | neg. | |
| Factor VIII | neg. | neg. | neg. | neg. | neg. | neg. | |
| IX | neg. | neg. | neg. | neg. | neg. | neg. | |
| XI | neg. | neg. | neg. | neg. | neg. | neg. | |
| XII | neg. | neg. | neg. | neg. | neg. | neg. | |
| CBC... | | | | | | | |
| WBC | 8.6 | 6.8 | 5.1 | 6.1 | 3.2 | 3.3 | Thous. |
| RBC | 4.12 | 3.78 | 5.22 | 5.99 | 5.22 | 5.59 | Millns. |
| HGB | 12.7 | 11.6 | 16.4 | 18.3 | 15.2 | 16.4 | g/dL. |
| HCT | 38.2 | 34.8 | 48.1 | 55.2 | 45.9 | 48.9 | % |
| MCV | 92.7 | 92.1 | 92.3 | 92.0 | 87.8 | 87.4 | fl. |
| MCH | 30.8 | 30.7 | 31.5 | 30.6 | 29.1 | 29.3 | pg. |
| MCHC | 33.2 | 33.4 | 34.1 | 33.2 | 33.1 | 33.6 | g/dL. |
| RDW | 12.0 | 11.1 | 12.8 | 12.5 | 14.5 | 14.8 | % |
| Platelets | 248 | 225 | 134. | 88 | 153 | 155 | Thous. |
| Differential | | | | | | | |
| Total polys | 60 | 64 | 66 | 76 | 64 | 66 | % |
| segs | 60 | 64 | 66 | 74 | 64 | 66 | % |
| bands | 0 | 0 | 0 | 2 | 0 | 0 | % |

TABLE II-continued
RESULTS: Human Blood From Normal, Healthy Volunteers

| | | | | | | | |
|---|---|---|---|---|---|---|---|
| lymphs | 29 | 30 | 2 | 7 | 21 | 26 | % |
| monos | 8 | 3 | 18 | 8 | 14 | 7 | % |
| eos | 3 | 1 | 11 | 7 | 21 | 26 | % |
| baso | 0 | 2 | 3 | 2 | 0 | 0 | % |
| Direct Coombs | neg. | neg. | neg. | neg. | neg. | neg. | |
| Serum Elect | | | | | | | |
| Albumin: | 62.80 | 64.16 | 62.11 | 64.52 | 57.05 | 56.27 | % |
| alpha 1-Glob | 3.27 | 3.58 | 3.61 | 3.42 | 3.63 | 3.41 | % |
| alpha 2-Glob | 10.24 | 9.73 | 11.59 | 10.86 | 8.15 | 8.33 | % |
| beta - Glob | 13.25 | 11.45 | 11.89 | 11.20 | 14.08 | 13.48 | % |
| gamma - Glob | 10.44 | 11.07 | 10.80 | 10.00 | 17.87 | 17.73 | % |

| Donor | RB | RB | |
|---|---|---|---|
| Date | 1/7/87 | 1/7/87 | |
| Time | 1140 | 1140 | hrs. |
| Light | no | yes | |
| Photofrin | 2.5 | 2.5 | ug/mL. |
| Sodium | 157.4 | 157.9 | mM |
| Potassium | 3.74 | 3.92 | mM |
| Calcium | 0.06 | 0.07 | mM |
| Glucose | 65 | 65 | mg/dL |
| | 63 | 62 | mg/dL |
| Osmotic Frag. | | | |
| Begin: | 0.46 | 0.46 | % |
| 50%: | 0.43 | 0.42 | % |
| complete: | 0.34 | 0.34 | % |
| Sugar Wat. lys | 0.000 | 0.006 | change in OD @ 540 nm: |
| Fibrinogen: | 298 | 237 | mg/dL. |
| PT: | 13.1 | 13.6 | secs. |
| APTT | 33.7 | 39.7 | secs. |
| Factor Def. Scn. | | | |
| Factor II | neg. | neg. | |
| Factor V | neg. | neg. | |
| Factor VII | neg. | neg. | |
| Factor X | neg. | neg. | |
| Factor VIII | neg. | neg. | |
| IX | neg. | neg. | |
| XI | neg. | neg. | |
| XII | neg. | neg. | |
| CBC . . . | | | |
| WBC | 3.0 | 3.2 | thous |
| RBC | 5.55 | 5.69 | millns |
| HGB | 16.3 | 16.9 | g/dL |
| HCT | 48.3 | 50.0 | % |
| MCV | 87.0 | 87.8 | fl. |
| MCH | 29.3 | 29.7 | pg. |
| MCHC | 33.6 | 33.7 | g/dL |
| RDW | 15.4 | 16.0 | % |
| Platelets | 150 | 139 | thous |
| Differential | | | |
| Total polys | 55 | 48 | % |
| segs | 55 | 48 | % |
| bands | 0 | 0 | % |
| lymphs | 26 | 24 | % |
| monos | 14 | 16 | % |
| eos | 3 | 2 | % |
| baso | 2 | 0 | % |
| Direct Coombs | neg. | polysp & IGgl+ wk C3dneg. | |
| Serum Elec.: | | | |
| Albumin | 56.52 | 56.15 | % |
| alpha 1-Glob | 3.66 | 3.43 | % |
| alpha 2-Glob | 8.12 | 8.23 | % |
| beta - Glob | 13.59 | 13.46 | % |
| gama - Glob | 18.10 | 18.74 | % |

*1 Sample hemolysed due to age of cuvet.
*2 CBC reflects inadequate loading of unopet since if the RBC had been low due to hemolysis the MCH would have risen to reflect the hemolysis.
Survival Studies: Blood smears prepared and examined for proteinacious debris: no unusual debris noted.

TABLE III

RESULTS: Human Blood Spiked With Herpes Simplex Virus Type I

| | | | |
|---|---|---|---|
| Donor | HS | HS | |
| Date | 1/12/87 | 1/12/87 | |
| Time | 0830 | 0830 | hrs. |
| Light | no | yes | |
| Photofrin | 0 | 2.5 | ug/mL. |
| Sodium | 159.2 | 159.8 | mM |
| Potassium | 4.15 | 3.97 | mM |
| Calcium | 0.07 | 0.07 | mM |
| Glucose | 56 | 61 | mg/dL |
| | 56 | 62 | mg/dL |
| Osmotic Frag. | | | |
| Begin: | 0.46 | 0.46 | % |
| 50%: | 0.44 | 0.44 | % |
| complete: | 0.36 | 0.34 | % |
| Sugar Wat. lys | 0 | 0 | OD @ 540 nm |
| Fibrinogen: | 336 | 377 | mg/dL. |
| PT: | 13.3 | 11.4 | secs. |
| APTT | 39.3 | 31.5 | secs. |
| Factor Def. Scn. | | | |
| Factor II | neg. | neg. | |
| Factor V | neg. | neg. | |
| Factor VII | neg. | neg. | |
| Factor X | neg. | neg. | |
| Factor VIII | neg. | neg. | |
| IX | neg. | neg. | |
| XI | neg. | neg. | |
| XII | neg. | neg. | |
| CBC ... | | | |
| WBC | 7.8 | 8.6 | thous |
| RBC | 5.09 | 5.25 | millns. |
| HGB | 15.9 | 16.3 | g/dL. |
| HCT | 47.3 | 48.8 | % |
| MCV | 92.6 | 92.7 | fl. |
| MCH | 31.3 | 31.0 | pg. |
| MCHC | 33.8 | 33.3 | g/dL. |
| RDW | 10.2 | 10.5 | % |
| Platelets | 221 | 193 | thous. |
| Differential | | | |
| Total polys | 78 | 78 | % |
| segs | 78 | 77 | % |
| bands | 0 | 1 | % |
| lymphs | 14 | 7 | % |
| monos | 6 | 11 | % |
| eos | 2 | 4 | % |
| baso | 0 | 0 | % |
| Direct Coombs | neg. | neg. | |
| Serum Elec.: | | | |
| Albumin | 62.52 | 64.68 | % |
| alpha 1-Glob | 2.85 | 2.81 | % |
| alpha 2-Glob | 10.32 | 10.54 | % |
| beta - Glob | 13.36 | 12.63 | % |
| gamma - Glob | 10.95 | 9.33 | % |
| Comments | | | |

TABLE IV

RESULTS: Human Blood From Patients With AIDS

| | | | | | |
|---|---|---|---|---|---|
| Donor | BL | BL | BDD | BD | |
| Date | 2/11/87 | 2/11/87 | 4/14/87 | 4/14/87 | |
| Time | 0925 | 0925 | 0900 | 0900 | hrs. |
| Light | no | yes | no | yes | |
| Photofrin | 0 | 2.5 | 0 | 2.5 | ug/mL. |
| Sodium | 152 | 155 | 160.7 | 163.0 | mM |
| Potassium | 3.8 | 3.8 | 3.32 | 3.43 | mM |
| Calcium | 0.10 | 0.007 | 0.06 | 0.06 | mM |
| Glucose | 75 | 75 | 66 | 67 | mg/dL |
| | | | 66 | 67 | mg/dL |
| Osmotic Frag. | | | | | |
| Begin: | 44 | 44 | 46 | 44 | % |
| 50%: | 44 | 42 | 41 | 41 | % |
| complete: | 34 | 34 | 34 | 34 | % |
| Sugar Wat. lys | 0.017 | 0.030 | 0.000 | 0.000 | OD @ 540 nm |
| Fibrinogen: | 378 | 315 | 227 | 183 | mg/dL. |
| PT: | 11.6 | 13.0 | 13.0 | 14.5 | secs. |
| APTT | 29.5 | 35.4 | 47.9 | 50.1 | secs. |
| Factor Def. Scn. | | | | | |
| Factor II | neg. | neg. | neg. | neg. | |
| Factor V | neg. | neg. | neg. | neg. | |
| Factor VII | neg. | neg. | neg. | neg. | |
| Factor X | neg. | neg. | neg. | neg. | |
| Factor VIII | neg. | neg. | neg. | neg. | |
| IX | neg. | neg. | neg. | neg. | |
| XI | neg. | neg. | neg. | neg. | |
| XII | neg. | neg. | neg. | neg. | |
| CBC ... | | | | | |
| WBC | 2.5 | 2.2 | 2.3 | 2.3 | thsnds. |
| RBC | 2.91 | 2.45 | 5.33 | 5.86 | millns. |
| HGB | 9.0 | 7.7 | 15.6 | 16.8 | g/dL. |
| HCT | 27.1 | 22.9 | 47.3 | 52.4 | % |
| MCV | 92.9 | 93.3 | 88.7 | 89.3 | fl. |
| MCH | 30.8 | 31.5 | 29.2 | 28.7 | pg. |
| MCHC | 33.5 | 33.7 | 33.0 | 32.1 | g/dL. |
| RDW | 9.2 | 9.1 | 11.6 | 11.9 | % |
| Platelets | 120 | 122 | 47 | 45 | thsnds. |
| Differential | | | | | |
| Total polys | 43 | 30 | 25 | 28 | % |
| segs | 35 | 54 | 20 | 21 | % |
| bands | 8 | 12 | 5 | 7 | % |
| lymphs | 39 | 54 | 36 | 31 | % |

TABLE IV-continued

RESULTS: Human Blood From Patients With AIDS

| Donor | BL | BL | BDD | BD | |
|---|---|---|---|---|---|
| Date | 2/11/87 | 2/11/87 | 4/14/87 | 4/14/87 | |
| Time | 0925 | 0925 | 0900 | 0900 | hrs. |
| Light | no | yes | no | yes | |
| Photofrin | 0 | 2.5 | 0 | 2.5 | ug/mL. |
| monos | 16 | 12 | 9 | 9 | % |
| eos | 2 | 4 | 30 | 30 | % |
| baso | 2 | 4 | 30 | 30 | % |
| Direct Coombs | neg (poly) specific | 1 + wk polysp. 1 + wkIgG C3 neg. sal. con — neg. | neg. | +/− 1 + IgG C3 neg. | |
| Serum Elect | | | | | |
| Albumin: | 46.34 | 42.93 | 48.77 | 52.61 | % |
| alpha 1-Glob | 3.17 | 2.73 | 3.07 | 3.14 | % |
| alpha 2-Glob | 12.42 | 12.01 | 9.10 | 7.51 | % |
| beta - glob | 14.22 | 21.46 | 13.90 | 13.16 | % |
| gamma - glob | 23.84 | 20.86 | 25.16 | 23.58 | % |
| O2 dissoc. | NR | NR | 28 | 25 | mm Hg at p50 |

Comments
Hemolysis of sample (LIPPBL) noted after approx. 2.5 ml. had been run through flow cell. Noted apparent high sed-rate of patient.

The abbreviations used in Tables II to IV are as follows:

| ABBREVIATION | FULL NAME |
|---|---|
| Photofrin | Photofrin II TM, from Johnson and Johnson, containing approximately 90% of dihematoporphyrin ether, DHE |
| Osmotic Frag | Osmotic Fragility |
| Sugar Wat. lys. | Sugar Water lysis tests |
| PT | Prothrombin Time |
| APTT | Activated Partial Thromboplastin Time |
| Factor Def. Scn. | Factor Deficiency Screen |
| CBC | Complete Blood Count |
| WBC | White Blood Cell |
| RBC | Red Blood Cell |
| HGB | Hemoglobin |
| HCT | Hematocrit |
| MCV | Mean Corpuscular Volume |
| MCH | Mean Corpuscular Hemoglobin Concentration |
| Total polys | Total polymorphonucleocytes |
| segs | segmented neutrophils |
| lymphs. | lymphocytes |
| monos. | monocytes |
| eosin | eosinophils |
| baso | basophils |
| Serum Elec | Serum Electrophoresis |
| Glob | Globulin |
| IgG | Immunoglobulin G |
| C3 | Complement fragment 3 |
| O2 dissoc. | Oxygen dissociation |
| sal. con | Saline concentration |
| neg. | Negative |
| NR | No result |
| sed-rate | sedimentation-rate |

The following abbreviated units are also used in Tables II to IV.

| ABBREVIATED UNITS | FULL NAME |
|---|---|
| hrs | hours |
| μg/ml | microgram per milliliter |
| mM | microgram per milliliter |
| mg/dl | milligram per deciliter |
| O.D. 540 | Optical Density at 540 nanometer |
| secs | seconds |
| Thous. | Thousand per microliter |
| Mill. | Millions per microliter |
| g/dL | gram per deciliter |
| fl. | femtoliter |
| pg | picogram |
| p | partial pressure |

It can be seen from these Tables that photo-irradiation in the presence of Photofrin II TM did not have a deleterious effect on blood. It is important in evaluating the data to appreciate the scaling down of normal laboratory procedures that occurred in these examples. The flow rate attained during these experiments was about 23 microliters per minute. Handling small aliquots on blood in a darkened room and avoiding them drying out presented logistical problems. In some control samples appreciable hemolysis occurred, this was found to arise from kinking of the cuvet tubing following repeated use in the high intensity light. This kinking caused pressure to build up in the sample, resulting in lysis. Whenever this problem arose the cuvet causing the problem was discarded. Viability of the irradiated samples containing Photofrin II TM was based on the following parameters: Potassium and glucose were well within the limits established for blood banked whole blood; RDW which is the standard deviation of red cell size was unchanged or lower than in the controls; mean corpuscular hemoglobin concentration (MCH) showed no elevation; osmotic fragility was unaffected; sugar water lysis tests showed no lysis following irradiation, but the same results are usually found in banked blood and is therefore not a contraindication for transfusing the blood. Serum electrophoresis could only be quantified as a percentage and not in absolute terms.

In two of the samples from patients with AIDS, prolongation of the APTT test occurred. One patient, however, had already had a prolonged APTT. In both these patients, the factor deficient screen test indicate that this prolongation did not arise from selective destruction of any of the coagulation factors but might have arisen from changes in the optical qualities of the plasma which could affect the optical clot detection devices.

In summary, photoirradiation of human blood outside the human body in the presence of a photoactive compound such as Photofrin TM did not affect the viability of the human blood as determined by currently accepted blood bank criteria.

Effect of Photofrin II ™ and Light on Human Whole Blood Containing *Herpes simplex* Virus Type I

*Herpes simplex* virus type I (HSV-I), the MacIntyre strain, was purchased from the American Type Culture Collection (ATCC) and propagated in Vero cells (ATCC) to a concentration of $10^6$–$10^7$ plaque forming units (PFU) per milliliter (ml). This solution was used as stock virus. Twenty milliliters of blood were collected from a healthy volunteer in acid citrate dextrose and the blood was divided into 0.9 ml aliquots. A volume of 0.1 ml of stock virus was added to eight separate aliquots of blood.

Photofrin ™ (From Johnson and Johnson. A photoactive dye that contains approximately 90% of pure dihematoporphyrin ether (DHE)), was added to duplicate tubes of the virus-blood mixture and a set of tubes containing blood only. The concentrations of Photofrin II ™ employed were 2.5, 10 and 20 µg/ml. Samples representing each concentration of Photofrin II ™ in the blood virus mixture were irradiated while moving through the flow cell by light at a wavelength of approximately 635 nm with an energy density of about 5 $J/cm^2$. Approximately 30–60 minutes elapsed between the addition of each concentration of Photofrin II ™ and exposure of light in the flow cell. During the holding period, the samples were maintained at 4° C. Except during the time of irradiation, all manipulations were carried out with minimal exposure to extraneous light. During a 15–30 minute period of time, approximately 0.7 ml of the irradiated sample was collected. A sample of virus mixed with blood but not containing Photofrin II ™ was also irradiated under the same conditions. During the holding period and the period of irradiation the duplicate samples of virus and blood containing different concentrations of Photofrin II ™ were held in the dark. In addition, samples of human blood (without virus) containing different concentrations of Photofrin II ™ and a sample of blood spiked with virus only were also maintained in the dark.

Each sample including the stock virus were assayed on vero cells for PFU/ml of HSV-I. The assay consisted of growing vero cells in minimal essential medium with Hanks balanced salt solution supplemented with 10% fetal bovine serum, L-glutamine and antibiotics. Herpes buffer (2%) was added for growth in open plates (twelve well microplates from Costar). Ten fold dilutions of each sample were prepared and 0.1 ml of the appropriate dilution for each individual sample was adsorbed at 37° C. for 1.5 hours on a cell monolayer from which the growth medium had been removed. After the adsorption period, the cell monolayer was washed and an overlay consisting of equal volumes of 2× strength L-15 medium and 2% methylcellulose was added. Following an appropriate incubation time at 37° C. (about 4 days), the overlay medium was removed. Monolayers were fixed with methanol and stained with giemsa to elaborate the presence of plaques. The plaques were counted using a dissecting microscope at a magnification of 20×.

The results of the experiment can be observed in Table V. It is clear that Photofrin II ™ in a concentration as low as 2.5 µg/ml, in combination with light at a wavelength of 625–635 nm having an energy density of 5 $J/cm^2$, achieved a near total (larger than 99.88%) kill of HSV-I in human whole blood. The use of larger amounts of Photofrin II ™ resulted in a similar reduction in viral infectivity. Blood samples containing the three different concentrations of Photofrin II ™ showed no evidence of cellular toxicity when assayed in the vero cells as described above.

TABLE V

PHOTOINACTIVATION OF BLOOD SPIKED WITH HERPES SIMPLEX TYPE-1 (HSV-1) CARRIED OUT IN A FLOW CELL SYSTEM

| Concentration of PII/ml | PFU/ml in Dark | PFU/ml in Light | % Reduction In PFU-Light to Dark |
|---|---|---|---|
| 2.5 µg | $1 \times 10^4$ | $1.2 \times 10^1$ | 99.88 |
| 10 µg | $9 \times 10^3$ | $1.25 \times 10^1$ | 99.86 |
| 20 µg | $9 \times 10^3$ | $0.5 \times 10^1$ | 99.94 |

PFU: Plaque forming unit;
PII: Photofrin II ™
HSV-1: Diluted 1:10 in blood and irradiated yielded $1 \times 10^4$ PFU/ml. Virus diluted in blood and not irradiated yielded $5 \times 10^4$ PFU/ml.

Effect of Photofrin II ™ and Light on Human Immunodeficiency Virus (HIV)

The human immunodeficiency virus (HIV) has also been irradiated in the flow cell. Approximately $4 \times 10^4$ infectious units (IU)/ml of cell-free HIV was prepared in tissue culture. The stock virus was then diluted 1:2 in tissue culture medium and six 1 ml aliquots of HIV were prepared. Irradiation studies were carried out in a similar manner as described above for the photoinactivation of HSV-I in blood. All samples were, however, maintained at room temperature throughout the experiment. One of the above aliquots of HIV was passed through the flow cell in the dark. A second aliquot of HIV was irradiated in the flow cell at 5 $J/cm^2$ for approximately 30 minutes which yielded approximately 0.7 ml of irradiated fluid. Three other samples, each containing different concentrations of Photofrin II ™, namely, 2.5, 10 and 20 µg/ml, were irradiated. All six samples were then placed in cell culture at five different dilutions: Neat (no dilution) $10^{-1}$, $10^{-2}$, $10^{-3}$, and $10^{-4}$. Supernatants from each culture were collected at prescribed intervals and assayed for HIV activity by the reverse transcriptase assay, according to the procedure reported by Chanh, et al. (Eur. Mol. Biol. Organization J., 5: 3065–3071, 1986).

It can be seen from Table VI that an appropriate amount of Photofrin II ™ in combination with light at a wavelength of 625–635 nm having an energy density of 5 $J/cm^2$ achieved a near complete kill of human immunodeficiency virus (HIV), the culprit for AIDS, in the flow cell.

TABLE VI

PHOTOINACTIVATION OF A CULTURE OF HUMAN IMMUNODEFICIENCY VIRUS IN A FLOW CELL SYSTEM[a]

| Concentration of PII/ml | Infectious Units Per Milliliter[b] | | % Kill In Light |
|---|---|---|---|
| | In Dark | In Light (5 J/cm2) | |
| 0 | $2 \times 10^4$ | $2 \times 10^4$ | 0 |
| 2.5 µg | — | C | C |
| 10 µg | — | $1^d$ | 100 |
| 20 µg | — | $1^d$ | 100 |

PII: Photofrin II ™
[a] The infectious units of the human immunodeficiency virus were unaffected whether or not the culture of virus was channelled through the flow cell system.
[b] As determined by reversed transcriptase activity.
C: Percent kill could not be determined.
[d] No detectable activity of the enzyme reverse transcriptase.

These studies suggest that the major target for photodynamic damage of Photofrin II ™ in viruses is envelope related.

The method of the present invention provides an effective and efficient means for eradicating infectious pathogenic contaminants from body fluids outside the body of an animal or a human.

Unlike the metabolic clearance of a photoactive drug in normal tissues observed in a live animal or human as described in the U.S. Pat. No. 4,649,151 to Dougherty et al., animal or human blood outside the body is not subject to this physiological or metabolic action by various body organs. Consequently, there is no mechanism for detoxification or "cleaning" of the human whole blood outside a body.

Suprisingly, despite the absence of the physiological or metabolic "cleansing" mechanism, human whole blood outside the human body shows a remarkable tolerance towards a photoactive compound such as Photofrin II ™. By all accounts, the human whole blood remains unchanged in the presence of certain concentrations of this photoactive compound. Equally surprising, external irradiation of normal human whole blood containing a photoactive compound with a specified wavelength of absorption causes no detectable damage to the whole blood when used at selected concentrations and intensity. Although outside the human body, after such treatment, the human whole blood is still unchanged by all currently acceptable standards. Although the infectious biological contaminants, such as parasites, bacteria or viruses encapsulated by a protein envelope, are totally different from human malignant tumor cells, a photoactive compound such as

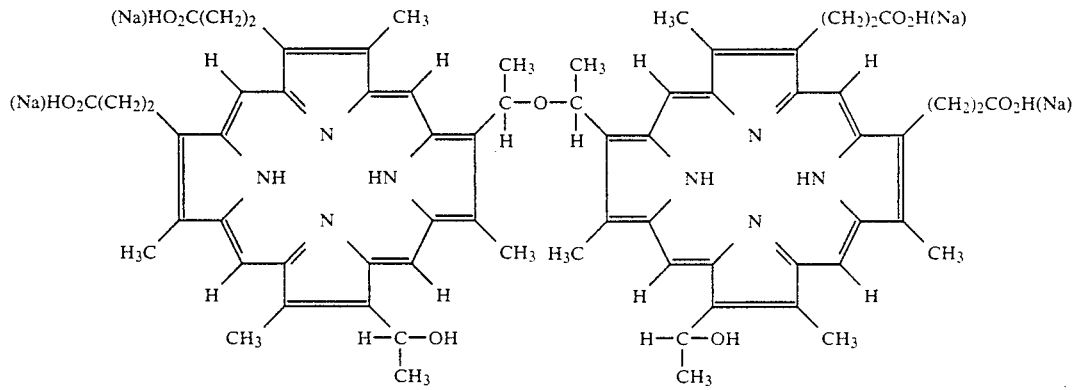

Photofrin II ™ has been found to have a selective affinity toward these infectious pathogenic contaminants contained in human whole blood outside the human body. Moreover, such a compound can be photoactivated outside the human body to cause the demise of these infectious biological pathogenic contaminants to which the compound has preferentially attached.

It is clear that the present invention is well adapted to carry out the objects and attain the ends and advantages mentioned herein as well as those inherent in the invention. While presently preferred embodiments of the invention have been described for purposes of this disclosure, numerous changes may be made which will readily suggest themselves to those skilled in the art and which are accomplished within the spirit of the invention disclosed and as defined in the appended claims.

We claim:

1. A method for eradicating infectious pathogenic biological contaminants from body fluid outside the body prior to introduction of the decontaminated body fluids into the body of a patient, said method comprising:

admixing an effective, non-toxic amount of a photoactive compound with the body fluid to produce a resulting body fluid, the photoactive compound having an affinity to be selectively bound to the contaminants;

maintaining the resulting body fluid in a suitable container in which there is no net mass transfer; and irradiating the resulting body fluid in the container with an effective level of essentially uniform intensity of radiation in the region of the visible spectrum, with a wavelength range of from about 400 nm to about 1000 nm, for an effective period of time such that the radiation penetrates the resulting fluid and exposes the photoactive-compound-bound contaminants to the radiation so as to eradicate such contaminants while maintaining the viability of said body fluids to produce viable decontaminated body fluids.

2. The method as recited in claim 1 further comprising the step of selecting a body fluid from the group consisting of whole blood, blood plasma, serum, and fluids from plasmapheresis.

3. The method as recited in claim 1 further comprising the step of selecting a body fluid comprising of semen.

4. The method as recited in claim 1 further comprising the step of selecting a photoactive compound comprising a mixture of porphyrins, at least a portion of the molecules of said porphyrin mixture having the molecular formula:

said molecules with said formula being fluorescent, photosensitizing, having the capability of selectively binding to said pathogenic biological contaminants, forming a high molecular weight aggregate with absorption peaks in the visible spectrum in water at approximately 365, 505, 537, 575, and 615 nanometers, absorption peaks in the infrared spectrum at approximately 3.0, 3.4, 6.4, 7.1, 8.1, 9.4, 12 and 15 microns, absorption peaks in carbon-13 nuclear magnetic resonance study at at least approximately 9.0, 18.9, 24.7, 34.5, 62, 94.5, 130–145, 171.7 ppm relative to a 37.5 ppm resonance peak of dimethyl sulfoxide and additional absorption peaks in carbon-13 nuclear magnetic resonance study at approximately 27.9 ppm and 68.4 ppm relative to the resonance peak of tetramethylsilane in deuterated chloroform solvent; and at least 50 percent of the porphyrins in said mixture being of said molecules having said molecular formula.

5. The method as recited in claim 4 wherein the amount of said mixture of porphyrins admixed with said fluid is from about 0.1 to about 50 micrograms per milliliter of body fluid.

6. The method as recited in claim 5 wherein the amount of said mixture of porphyrins admixed with said fluid is from about 2 to 50 micrograms per milliliter of body fluid.

7. The method as recited in claim 1 wherein the level of radiation is produced by a light source having a wavelength of from about 400 to about 1000 nm and an energy density of from about 0.1 to about 50 J/cm$^2$.

8. The method as recited in claim 7 wherein the level of radiation is produced by a light source having a wavelength of from about 600 to about 700 nm and an energy density from about 1 to about 20 J/cm$^2$.

9. The method as recited in claim 1 further comprising the step of selecting body fluid which contains pathogenic biological contaminants comprising an envelope-containing virus.

10. The method as recited in claim 9 further comprising the step of selecting the envelope-containing virus from the group consisting of Herpesviridae, Poxviridae, Iridoviridae, Hepadnaviridae, Orthomyxoviridae, and Paramyxoviridae.

11. The method as recited in claim 9 further comprising the step of selecting the envelope-containing virus from the group consisting of Rhabdoviridae, Bunyaviridae, Filoviridae, Nodaviridae, and Togaviridae.

12. The method as recited in claim 9 further comprising the step of selecting the envelope-containing virus from the group consisting of Flaviviridae, Retroviridae, and Arenaviridae.

13. The method as recited in claim 12 further comprising the step of selecting the Retroviridae comprising a human immunodeficiency virus.

14. The method as recited in claim 1 further comprising the step of selecting body fluid which contains pathogenic biological contaminants comprising a bacteria selected from the group consisting of *Streptococcus faecalis* and *Bacillus subtilis*.

15. The method as recited in claim 1 further comprising the step of selecting body fluid which contains pathogenic biological contaminants comprising a *Borrelia burgdorferi* bacteria.

16. The method as recited in claim 1 further comprising the step of selecting body fluid which contains pathogenic biological contaminants comprising a malarial parasite.

17. The method as recited in claim 1 further comprising the step of selecting body fluid which contains pathogenic biological contaminants comprising a trypanosomal parasite.

18. The method as recited in claim 1 further comprising the step of agitating the resulting body fluid in the container.

19. The method as recited in claim 18 wherein the step of agitating is carried out by moving the container.

20. The method as recited in claim 18 wherein the step of agitating is carried out by the aid of an agitating means.

21. The method as recited in claim 20 wherein said agitating means comprises an agitating object.

22. The method as recited in claim 1 wherein said container is kept static.

23. A method for externally purifying a blood product to eradicate pathogenic biological contaminants selected from the group consisting of envelope-containing viruses, bacteria, malarial, and trypanosomal parasites prior to introduction of the decontaminated blood products intravenously into a patient, said method comprising:

admixing an effective amount of a photoactive compound with the blood products to bind the contaminant with the photoactive compound, said photoactive compound comprising a mixture of porphyrins, at least a portion of the molecules of said porphyrin mixture having the molecular formula:

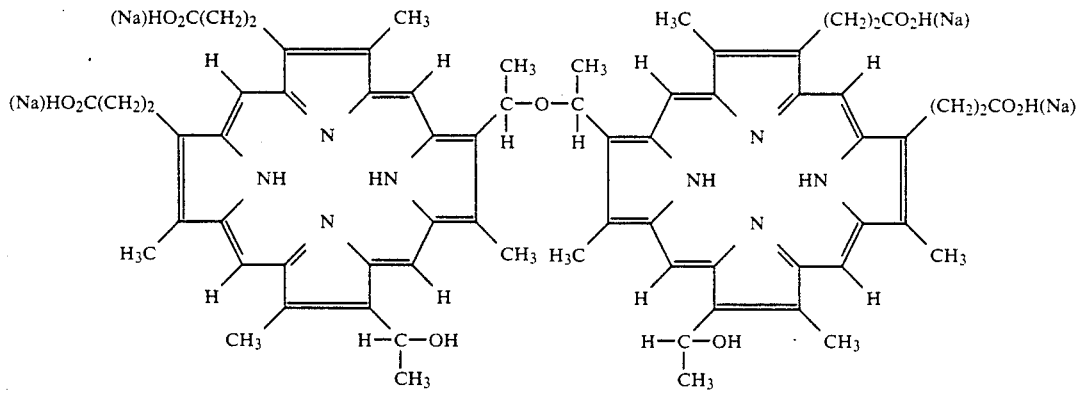

said molecules with said formula being fluorescent, photosensitizing, having the capability of selectively binding to said pathogenic biological contaminants, forming a high molecular weight aggregate with absorption peaks in the visible spectrum in water at approximately 365, 505, 537, 575, and 615 nanometers, absorption peaks in the infrared spectrum at approximately 3.0, 3.4, 6.4, 7.1, 8.1, 9.4, 12 and 15 microns, absorption peaks in carbon-13 nuclear magnetic resonance study at at least approximately 9.0, 18.9, 24.7, 34.5, 62, 94.5, 130–145, 171.7 ppm relative to a 37.5 ppm resonance peak of dimethyl sulfoxide and additional absorption peaks in carbon-13 nuclear magnetic resonance study at approximately 27.9 ppm and 68.4 ppm relative to the resonance peak of tetramethylsilane in deuterated chloroform solvent; and at least 50 percent of the porphyrins in said mixture being of said molecules having said molecular formula;

maintaining the blood product containing the porphyrins-bound contaminants in a suitable container, exposable to a radiation source capable of irradiating the blood product and in which there is no net mass transfer; and irradiating the blood product in the container with an essentially uniform intensity of radiation source in the region of visible spectrum, with a wavelength of from about 400 nm to about 1000 nm for an effective period of time to permit the radiation to penetrate through the blood product in the container and eradicate the contaminants while maintaining the viability of components in said blood product.

24. The method as recited in claim 23 wherein the amount of said mixture of porphyrins admixed with said blood product is from about 0.1 to about 50 micrograms per milliliter of blood product.

25. The method as recited in claim 24 wherein the amount of said mixture of porphyrins admixed with said blood product is from about 2 to about 50 micrograms per milliliter of blood product.

26. The method as recited in claim 23 wherein the level of radiation is produced by a light source having a wavelength of from about 400 to about 700 nm and an energy density of from about 0.1 to about 50 J/cm$^2$.

27. The method as recited in claim 26 wherein the level of radiation is produced by a light source having a wavelength of from about 600 to about 700 nm and an energy density of from about 1 to about 20 J/cm$^2$.

28. The method as recited in claim 23 further comprising the step of selecting blood product which contains pathogenic biological contaminants comprising an envelope-containing virus.

29. The method as recited in claim 28 further comprising the step of selecting the envelope-containing virus from the group consisting of Herpesviridae, Poxviridae, Iridoviridae, Hepadnaviridae, Orthomyxoviridae, and Paramyxoviridae.

30. The method as recited in claim 28 further comprising the step of selecting the envelope-containing virus from the group consisting of Rhabdoviridae, Bunyaviridae, Filoviridae, Nodaviridae, and Togaviridae.

31. The method as recited in claim 28 further comprising the step of selecting the envelope-containing virus from the group consisting of Flaviviridae, Retroviridae, and Arenaviridae.

32. The method as recited in claim 31 further comprising the step of selecting the Retroviridae comprising a human immunodeficiency virus.

33. The method as recited in claim 23 further comprising the step of selecting blood product which contains pathogenic biological contaminants comprising a bacteria selected from the group consisting of *Streptococcus faecalis* and *Bacillus subtilis*.

34. The method as recited in claim 23 further comprising the step of selecting body fluid which contains pathogenic biological contaminants comprising a *Borrelia burgdorferi* bacteria.

35. The method as recited in claim 23 further comprising the step of selecting blood product which contains pathogenic biological contaminants comprising a malarial parasite.

36. The method as recited in claim 23 further comprising the step of selecting blood product which contains pathogenic biological contaminants comprising a trypanosomal parasite.

37. The method as recited in claim 23 further comprising the step of agitating the resulting body fluid in the container.

38. The method as recited in claim 37 wherein the step of agitating is carried out by moving the container.

39. The method as recited in claim 37 wherein the step of agitating is carried out by the aid of an agitating means.

40. The method as recited in claim 39 wherein said agitating means comprises an agitating object.

41. The method as recited in claim 23 wherein said container is kept static.

42. A method for extracorporeal treatment of the blood of a patient infected with infectious pathogenic biological contaminants said method comprising;

removing blood from the body of a patient infected with infectious pathogenic biological contaminants;

adding to said blood an effective, non-toxic amount of photoactive compound having an affinity to be selectively bound to the infectious contaminants;

maintaining said treated blood in a suitable container in which there is not net mass transfer;

irradiating said contaminated blood admixed with photo-active compound in the container with an effective level of essentially uniform intensity of radiation in the region of visible spectrum, with a wavelength range of from about 400 nm to about 1000 nm, for an effective period of time such that the radiation penetrates the blood and exposes the photoactive-compound-bound infectious contaminants to the radiation so as to eradicate such infectious contaminants while maintaining the viability of components in said blood to produce a viable and decontaminated blood; and returning said viable and decontaminated blood to the patient's body.

43. The method as recited in claim 42 further comprising the step of selecting a photoactive compound comprising a mixture of porphyrins, at least a portion of the molecules of said porphyrin mixture having the molecular formula:

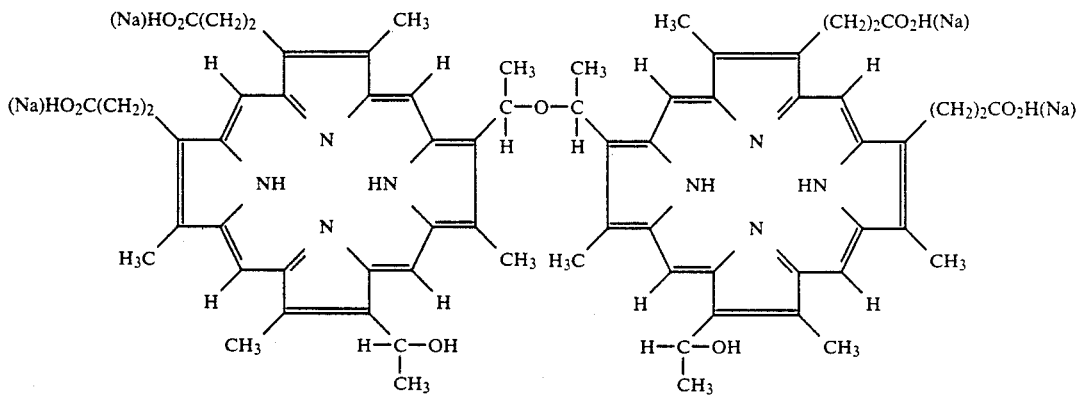

said molecules with said formula being fluorescent, photosensitizing, having the capability of selectively binding to said pathogenic biological contaminants, forming a high molecular weight aggregate with absorption peaks in the visible spectrum in water at approximately 365, 505, 537, 575, and 615 nanometers, absorption peaks in the infrared spectrum at approximately 3.0, 3.4, 6.4, 7.1, 8.1, 9.4, 12 and 15 microns, absorption peaks in carbon-13 nuclear magnetic resonance study at at least approximately 9.0, 18.9, 24.7, 34.5, 62, 94.5, 130–145, 171.7 ppm relative to a 37.5 ppm resonance peak of dimethyl sulfoxide and additional absorption peaks in carbon-13 nuclear magnetic resonance study at approximately 27.9 ppm and 68.4 ppm relative to the resonance peak of tetramethylsilane in deuterated chloroform solvent; and at least 50 percent of the porphyrins in said mixture being of said molecules having said molecular formula.

44. The method as recited in claim 43 further comprising the step of administering said mixture of porphyrins to the patient prior to the removal of the blood from the patient's body for irradiation.

45. The method as recited in claim 44 further comprising the step of administering said mixture of porphyrins to the patient between about thirty minutes and about one week prior to removal of the patient's blood for irradiation.

46. The method as recited in claim 44 further comprising the step of administering said mixture of porphyrins at a dosage from about 0.5 mg to about 40 mg per kg of body weight of the patient.

47. The method as recited in claim 42 further comprising the step of admixing said mixture of porphyrins with said blood in an amount from about 0.1 to about 50 micrograms per milliliter of said blood.

48. The method as recited in claim 47 further comprising the step of admixing said mixture of porphyrins with said blood in an amount from about 2 to about 50 micrograms per milliliter of said blood.

49. The method as recited in claim 42 wherein the level of radiation is produced by a light source having a wavelength of from about 600 to about 1000 nm and an energy density of from about 1 to about 50 J/cm$^2$.

50. The method as recited in claim 49 wherein the level of radiation is produced by a light source having a wavelength of from about 600 to about 700 nm and an energy density of from about 1 to about 20 J/cm$^2$.

51. The method as recited in claim 42 further comprising the step of selecting a blood which contains pathogenic biological contaminants comprising an envelope-containing virus.

52. The method as recited in claim 51 further comprising the step of selecting the envelope-containing virus from the group consisting of Herpesviridae, Poxviridae, Iridoviridae, Hepadnaviridae, Orthomyxoviridae, and Paramyxoviridae.

53. The method as recited in claim 51 further comprising the step of selecting the envelope-containing virus from the group consisting of Rhabdoviridae, Bunyaviridae, Filoviridae, Nodaviridae, and Togaviridae.

54. The method as recited in claim 51 further comprising the step of selecting the envelope-containing virus from the group consisting of Flaviviridae, Retroviridae, and Arenaviridae.

55. The method as recited in claim 54 further comprising the step of selecting the Retroviridae comprising a human immunodeficiency virus.

56. The method as recited in claim 42 further comprising the step of selecting a blood which contains pathogenic biological contaminants comprising a bacteria selected from the group consisting of *Streptococcus faecalis* and *Bacillus subtilis*.

57. The method as recited in claim 42 further comprising the step of selecting body fluid which contains pathogenic biological contaminants comprising a *Borrelia burgdorferi* bacteria.

58. The method as recited in claim 42 further comprising the step of selecting the pathogenic biological contaminants comprising a malarial parasite.

59. The method as recited in claim 42 further comprising the step of selecting a blood which contains pathogenic biological contaminants comprising a trypanosomal parasite.

60. The method as recited in claim 42 further comprising the step of agitating the resulting body fluid in the container.

61. The method as recited in claim 60 wherein the step of agitating is carried out by moving the container.

62. The method as recited in claim 60 wherein the step of agitating is carried out by the aid of an agitating means.

63. The method as recited in claim 62 wherein said agitating means comprises an agitating object.

64. The method as recited in claim 42 wherein said container is kept static.

65. A method for extracorporeal treatment of the blood of a patient infected with infectious pathogenic biological contaminants said method comprising:

administering to the patient infected with infectious pathogenic foreign biological contaminants an effective, non-toxic amount of photoactive compound having an affinity to be selectively bound to the infectious contaminants;

waiting a period of time for the photoactive compound to be taken up by the blood;

removing the blood from the body of the patient;

maintaining the blood in a suitable container in which there is no net mass transfer;

irradiating the blood admixed with photoactive compound in the container with an effective level of essentially uniform intensity of radiation in the region of visible spectrum, with a wavelength range of from about 400 nm to about 1000 nm, for an effective period of time such that the radiation penetrates the blood and exposes the photoactive-compound-bound infectious contaminants to the radiation so as to eradicate such infectious contaminants while maintaining the viability of components in said blood to produce a viable and decontaminated blood; and returning the viable and decontaminated blood to the patient's body.

66. The method as recited in claim 65 wherein the waiting period of time is from about one hour to about one week.

* * * * *